US012616644B2

(12) United States Patent
Isaacman et al.

(10) Patent No.: US 12,616,644 B2
(45) **Date of Patent: *May 5, 2026**

(54) POLYURETHANE GELS

(71) Applicant: GRANT INDUSTRIES, INC., Elmwood Park, NJ (US)

(72) Inventors: Michael J. Isaacman, New York, NY (US); Anna K. Croom, Brooklyn, NY (US); Ronald V. Lerum, Leonia, NJ (US); John Gormley, Midland Park, NJ (US)

(73) Assignee: GRANT INDUSTRIES, INC., Elmwood Park, NJ (US)

( * ) Notice: Subject to any disclaimer, the term of this patent is extended or adjusted under 35 U.S.C. 154(b) by 747 days.

This patent is subject to a terminal disclaimer.

(21) Appl. No.: 17/625,964

(22) PCT Filed: Jul. 10, 2020

(86) PCT No.: PCT/US2020/041540

§ 371 (c)(1),
(2) Date: Jan. 10, 2022

(87) PCT Pub. No.: WO2021/007489

PCT Pub. Date: Jan. 14, 2021

(65) Prior Publication Data

US 2022/0378670 A1 Dec. 1, 2022

Related U.S. Application Data

(60) Provisional application No. 63/018,859, filed on May 1, 2020, provisional application No. 62/872,592, filed on Jul. 10, 2019, provisional application No. 62/872,588, filed on Jul. 10, 2019.

(51) Int. Cl.

| | |
|---|---|
| ***A61K 8/04*** | (2006.01) |
| ***A61K 8/87*** | (2006.01) |
| ***A61K 9/06*** | (2006.01) |
| ***A61Q 19/00*** | (2006.01) |
| ***C08G 18/10*** | (2006.01) |
| ***C08G 18/22*** | (2006.01) |
| ***C08G 18/34*** | (2006.01) |
| ***C08G 18/36*** | (2006.01) |
| ***C08G 18/73*** | (2006.01) |
| ***C08G 18/75*** | (2006.01) |

(52) U.S. Cl.

CPC ................ *A61K 8/042* (2013.01); *A61K 8/87* (2013.01); *A61K 9/06* (2013.01); *A61Q 19/00* (2013.01); *C08G 18/10* (2013.01); *C08G 18/227* (2013.01); *C08G 18/345* (2013.01); *C08G 18/348* (2013.01); *C08G 18/36* (2013.01); *C08G 18/73* (2013.01); *C08G 18/755* (2013.01); *A61K 2800/48* (2013.01); *A61K 2800/805* (2013.01)

(58) Field of Classification Search

CPC . A61K 8/042; A61K 8/87; A61K 9/06; A61K 2800/48; A61K 2800/805; A61Q 19/00; C08G 18/10; C08G 18/227; C08G 18/345; C08G 18/348; C08G 18/36; C08G 18/73; C08G 18/755

See application file for complete search history.

(56) References Cited

U.S. PATENT DOCUMENTS

| | | | | |
|---|---|---|---|---|
| 3,192,185 | A | 6/1965 | Achterhof et al. | |
| 3,627,719 | A * | 12/1971 | Sellet ................. | D06M 15/564 524/391 |
| 4,404,296 | A | 9/1983 | Dietmar | |
| 4,661,099 | A | 4/1987 | Von Bittera et al. | |
| 5,284,897 | A | 2/1994 | Columbus et al. | |
| 5,908,631 | A | 6/1999 | Arnaud et al. | |
| 7,799,874 | B2 | 9/2010 | Carr et al. | |
| 8,222,363 | B2 | 7/2012 | Lin et al. | |
| 9,376,404 | B2 | 6/2016 | Nakagawa et al. | |
| 9,610,237 | B2 | 4/2017 | Burgo et al. | |
| 10,035,871 | B2 | 7/2018 | Langer et al. | |
| 2003/0092932 | A1 | 5/2003 | Tong et al. | |

(Continued)

FOREIGN PATENT DOCUMENTS

| | | | |
|---|---|---|---|
| EP | 1142959 | A1 | 10/2001 |
| EP | 2365024 | A1 | 9/2011 |

(Continued)

OTHER PUBLICATIONS

Aguilar-Castro et al., "Biobased polyester obtained from bifunctional monomers through metathesis of fatty acids as precursor to synthesis of polyurethanes." J. Appl. Polym. Sci., 136: 47095 (2018).

Mutlu et al., "Castor oil as a renewable resource for the chemical industry." Eur. J. Lipid Sci. Technol., 112: 10-30 (2010).

Srivastava et al., "Gel Point Prediction of Metal-filled Castor Oil-based Polyurethanes System." Polym. Adv. Technol., 13: 1055-1066 (2002).

International Search Report issued in International Application No. PCT/US2020/041540, mailed Oct. 16, 2020.

Jones, Charla, "What Is Coco-Caprylate Doing in My Natural Skin Care Products?" Eu2Be (May 8, 2015): pp. 1-2 <https://eu2be.com/blogs/discover/19389252-what-is-coco-caprylate-doing-in-my-natural-skin-care-products>; p. 2.

(Continued)

*Primary Examiner* — Shirley V Gembeh

(74) *Attorney, Agent, or Firm* — LUCAS & MERCANTI, LLP

(57) ABSTRACT

The present invention relates to gel compositions comprising a polyurethane elastomer. The polyurethane elastomer is formed from the reaction of a polyol, a polyisocyanate, and optionally a polyurethane reaction catalyst, optionally in the presence of a topically acceptable carrier fluid. In some embodiments, the gel composition comprises a personal active ingredient or a healthcare active ingredient, which may be incorporated into the gel composition via a pre-load method or a post-load method. Also provided herein are gel pastes and topical formulations comprising the polyurethane elastomers, and methods of making the same.

13 Claims, 5 Drawing Sheets

(56) References Cited

U.S. PATENT DOCUMENTS

| | | | |
|---|---|---|---|
| 2005/0276770 | A1 | 12/2005 | Filippi et al. |
| 2008/0287604 | A1 | 11/2008 | Wibaux |
| 2009/0081137 | A1 | 3/2009 | Nguyen Kim et al. |
| 2009/0232752 | A1 | 9/2009 | Carson et al. |
| 2011/0014139 | A1 | 1/2011 | Viala et al. |
| 2011/0045983 | A1 | 2/2011 | Healy et al. |
| 2012/0046358 | A1 | 2/2012 | Cheng et al. |
| 2012/0270992 | A1 | 10/2012 | Larock et al. |
| 2013/0079486 | A1 | 3/2013 | Hidesaki et al. |
| 2013/0149260 | A1 | 6/2013 | Delvalle et al. |
| 2015/0128335 | A1 | 5/2015 | Dehni |
| 2015/0197610 | A1 | 7/2015 | Peterson et al. |
| 2016/0067153 | A1 | 3/2016 | Chen et al. |
| 2018/0079852 | A1 | 3/2018 | Hecking et al. |
| 2018/0208720 | A1 | 7/2018 | Hasegawa et al. |
| 2018/0311140 | A1 | 11/2018 | Perner et al. |
| 2018/0369125 | A1 | 12/2018 | Woodland et al. |
| 2018/0371149 | A1 | 12/2018 | Langer et al. |
| 2019/0169390 | A1 | 6/2019 | Peterson et al. |

FOREIGN PATENT DOCUMENTS

| | | | | |
|---|---|---|---|---|
| EP | 2380557 | A1 | | 10/2011 |
| EP | 2759572 | A1 | | 7/2014 |
| EP | 3778689 | A1 | | 2/2021 |
| EP | 3778690 | A1 | | 2/2021 |
| JP | H04320457 | A | | 11/1992 |
| JP | H05262622 | A | | 10/1993 |
| JP | 2000313731 | A | | 11/2000 |
| JP | 3631542 | B2 | | 3/2005 |
| JP | 2008201698 | A | | 9/2008 |
| JP | 2008239542 | A | | 10/2008 |
| JP | 2008260722 | A | | 10/2008 |
| JP | 2011178693 | A | | 9/2011 |
| JP | 2017114773 | A | | 6/2017 |
| JP | 2018090662 | | * | 6/2018 |
| JP | 2018090662 | A | | 6/2018 |
| JP | 2018199653 | A | | 12/2018 |
| JP | 6892253 | B2 | | 6/2021 |
| WO | 2008039466 | A1 | | 4/2008 |
| WO | 2013074655 | A1 | | 5/2013 |
| WO | 2014167518 | A1 | | 10/2014 |
| WO | 2016090081 | A1 | | 6/2016 |
| WO | 2018122532 | A1 | | 7/2018 |
| WO | 2018183440 | A1 | | 10/2018 |
| WO | 2021007489 | A1 | | 1/2021 |
| WO | 2021231527 | A1 | | 11/2021 |
| WO | 2021257937 | A1 | | 12/2021 |

OTHER PUBLICATIONS

International Search Report and Written Opinion for International Application No. PCT/US2020/046170 (10 Pages) (Nov. 18, 2020).

International Preliminary Report on Patentability for International Application No. PCT/US2020/046170 (9 Pages) (Mar. 10, 2022).

Written Opinion corresponding to PCT/US2020/041540 (14 Pages) (Oct. 16, 2020).

Becker et al., "Safety Assessment of Polyurethanes as Used in Cosmetics,", Cosmetic Ingredient Review, pp. 1-96., 2017.

Extended European Search Report for Corresponding European Application No. 20855942.7, Nov. 8, 2023, 13 Pages.

Hamid Yeganeh, et al., "Preparation and properties of novel biodegradable polyurethane networks based on castor oil and poly(ethylene glycol)" Polymer Degradation and Stability, vol. 92, pp. 480-489, 2007.

* cited by examiner

Biolastomer Compatibility with Common Carriers

| | Biolastomer A (12.5%) | | Biolastomer C (11%) | | Biolastomer D (14%) | | Velvesil DM (17.5%) | | DOWSIL 9040 (12%) | |
|---|---|---|---|---|---|---|---|---|---|---|
| **Wt% emollients** | **20%** | **30%** | **20%** | **30%** | **20%** | **30%** | **10%** | **20%** | **20%** | **30%** |
| Triglycerides | Clarity<br>Gel strength | Clarity<br>Gel strength | Clarity<br>Gel strength | Clarity<br>Gel strength | Clarity<br>Gel strength | Clarity<br>Gel strength | Clarity<br>Gel strength | Clarity<br>Gel strength | Clarity<br>Gel strength | Clarity<br>Gel strength |
| Caprylic/capric triglyceride | Translucent<br>5 | Hazy<br>1 | Hazy<br>3 | Hazy<br>1 | Hazy<br>3 | Hazy<br>3 | Not Compatible | Not Compatible | Clear<br>1 | Compatible |
| Esters | | | | | | | | | | |
| Isopropyl palmitate | Hazy<br>3 | Hazy<br>1 | Hazy<br>2 | Hazy<br>2 | Hazy<br>1 | Not Compatible | Not Compatible | Not Compatible | Clear<br>3 | Not Compatible |
| Fatty alcohol | | | | | | | | | | |
| Octyl dodecanol | Translucent<br>5 | Hazy<br>1 | Translucent<br>5 | Hazy<br>1 | Translucent<br>5 | Translucent<br>5 | Not Compatible | Not Compatible | Not Compatible | Not Compatible |
| Hydrophilics | | | | | | | | | | |
| EtOH | Translucent<br>5 | Hazy<br>2 | Translucent<br>5 | Hazy<br>3 | Translucent<br>5 | Translucent<br>5 | TBD | Not Compatible | TBD | TBD |
| Hydrocarbons | | | | | | | | | | |
| Hemisqualane | Hazy<br>1 | Hazy<br>1 | Hazy<br>1 | Not Compatible | Not Compatible | Not Compatible | Not Compatible | Not Compatible | Clear<br>3 | Not Compatible |
| Silicones | | | | | | | | | | |
| Dimethicone 350 cst | Not Compatible | Not Compatible | Not Compatible | Not Compatible | Not Compatible | Not Compatible | Not Compatible | Not Compatible | Clear<br>1 | Compatible |

FIG. 1

POLYURETHANE GELS

FIELD OF THE INVENTION

The present invention relates to gel compositions comprising a polyurethane elastomer.

BACKGROUND OF THE INVENTION

Elastomer gels consist of a cross-linked three-dimensional polymer network suspended in an emollient. Elastomer gels are capable of swelling in emollients and are useful as oil phase thickeners in cosmetic formulations. These elastomer gels have a ball bearing-like feel on skin and provide for enhanced aesthetics and feel. These desirable attributes cannot be achieved with traditional oil gels or linear polymers, making elastomer gels unique cosmetic application vehicles.

Silicone elastomer gels are widely utilized ingredients in personal care products for their thickening and gelling efficiency, and unique silky and powdery sensory profile. When incorporated into formulations they provide a smooth, dry, and non-oily feel. Silicone elastomers are compatible with silicone-based fluids. Recently, concerns have been raised regarding the negative environmental impact of silicone-based ingredients in personal care products. Silicones are resistant to oxidative and chemical attack and are therefore not biodegradable. In addition, silicones are sourced from fossil fuels and are not considered to be a renewable resource. As consumers become increasingly educated with the environmental impact of cosmetics, the demand for biodegradable and renewably sourced ingredients that are silicone-free has rapidly increased.

Silicone replacements derived from biomass have begun to enter the personal care market to meet these demands. However, these linear polymers and emollients do not provide the unique aesthetics that elastomer gels provide. Therefore, a need exists for a silicone-free elastomer gel that has a favorable environmental profile.

The present invention consists of a polyurethane elastomer gel that is silicone-free and comprised of >99% bio-based materials. The polyurethane elastomer gel provides the aesthetic benefits of silicone-based elastomers while meeting a market demand for renewably sourced materials that are silicone-free.

The invention further relates to a method for preparing the polyurethane elastomer gel. A bio-based polyol is reacted with a bio-based polyisocyanate using a polyurethane catalyst at elevated temperature in a reaction medium of bio-based emollient or a mixture of bio-based emollients to give a polyurethane elastomer rubber. A bio-based emollient is then added to the rubber, and the mixture is processed into a polyurethane elastomer gel.

SUMMARY OF THE INVENTION

In some embodiments, the invention provides a gel composition comprising a polyurethane elastomer requiring no purification and formed in a topically acceptable solvent from the reaction of: A) a polyol; B) a polyisocyanate; C) an optional polyurethane reaction catalyst; and D) a topically acceptable carrier fluid.

In embodiments, a personal care or healthcare active ingredient (E) is incorporated into the polyurethane elastomer gel by dissolving it in the topically acceptable carrier fluid during the formation of the polyurethane elastomer gel (pre-load method) or admixing it with a formed polyurethane elastomer gel (post-load method).

In further embodiments, the invention further provides a cross-linked polyurethane elastomer network with the following general structure:

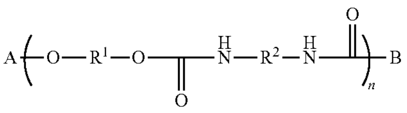

wherein: n is 2 to 10000000; A is an end group selected from a hydrogen, an isocyanate and a hydroxyl; $R^1$ is a C1-C60 substituted or unsubstituted linear or branched aliphatic group, cycloaliphatic group, aryl group, heterocycloaliphatic group, or heteroaryl group, optionally comprising a heteroatom; $R^2$ is a C1-C60 substituted or unsubstituted linear or branched aliphatic group, cycloaliphatic group, aryl group, heterocycloaliphatic group, or heteroaryl group, optionally comprising a heteroatom; and B is an end group selected from an isocyanate and a hydroxyl.

In some embodiments, the invention provides a cross-linked polyurethane elastomer network according to the following general reaction scheme:

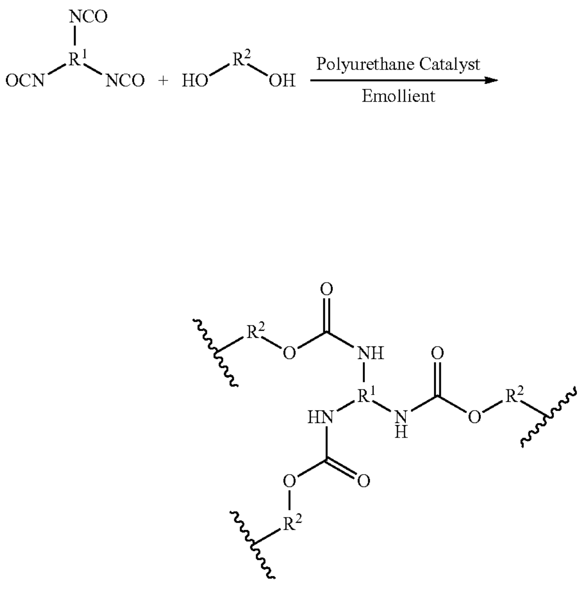

where R is a polyol with two or more functional groups and where $R^1$ is an isocyanate with three or more functional groups, and the emollient is topically acceptable.

In further embodiments, the invention provides a cross-linked polyurethane elastomer network according to the following general reaction scheme:

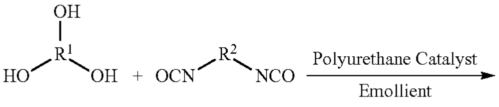

-continued
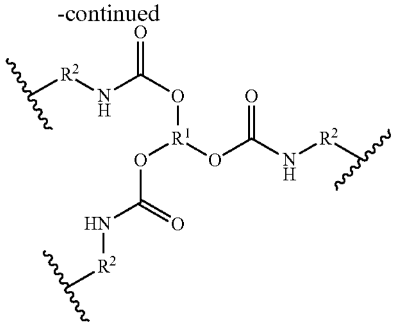
where R is a polyol with three or more functional groups and where $R^1$ is an isocyanate with two or more functional groups, and the emollient is topically acceptable.
In further embodiments, the invention provides a cross-linked polyurethane elastomer network according to the following general reaction scheme:
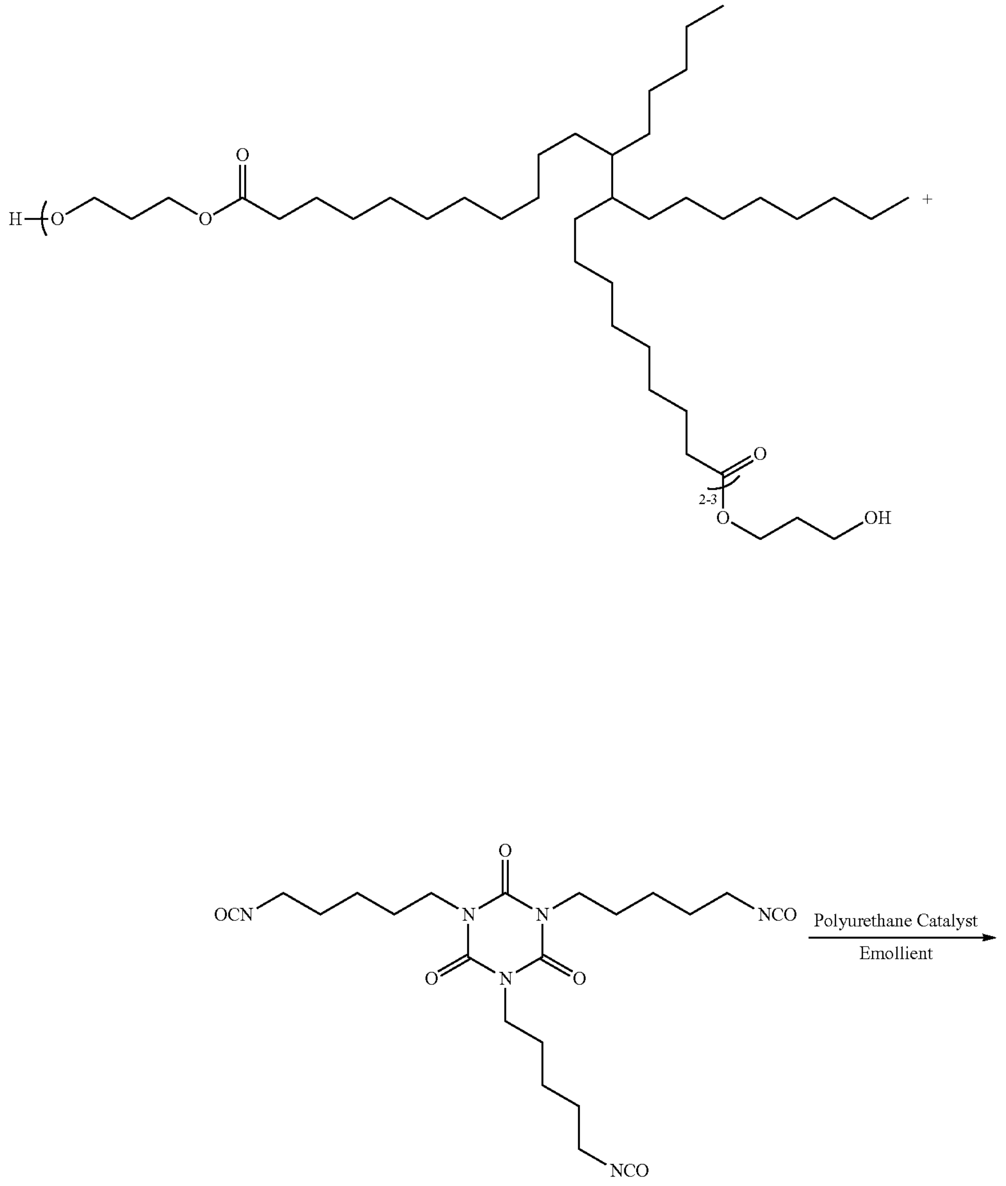

-continued

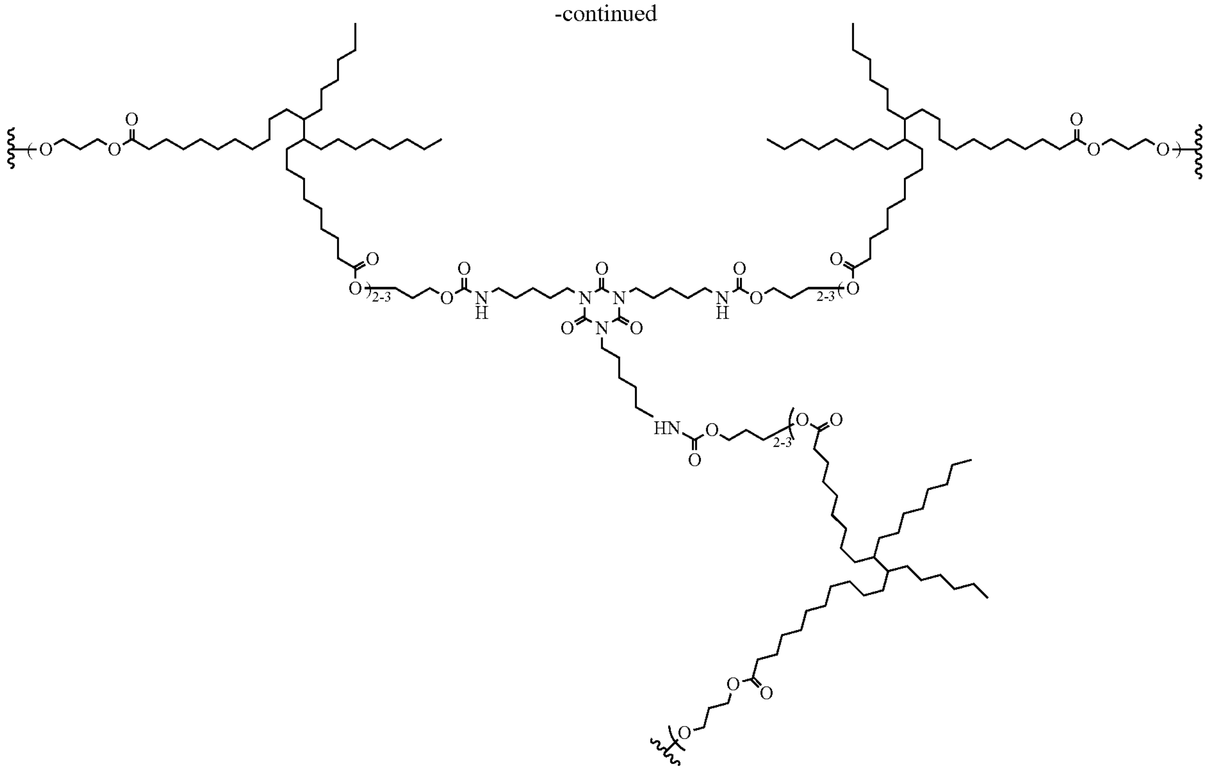

where the emollient is topically acceptable.

In still further embodiments, the invention provides a process for making a polyurethane elastomer gel comprising: Adding to a container a cosmetically acceptable emollient, polyol, and polyisocyanate; stirring the mixture at room temperature until a clear, homogeneous solution is obtained; adding a polyurethane catalyst with stirring, and heating the reaction to about 60° C. for about 23 hours, at which point a soft rubber is formed; allowing the rubber to cool to room temperature, and adding a cosmetically acceptable emollient and processing the mixture into a smooth gel.

In embodiments, the rubber is formed at room temperature. In embodiments, the polyol, polyisocyanate and emollient are bio-based. In embodiments, the polyol, polyisocyanate and emollient are not bio-based. In embodiments, a bismuth, tin, zinc, or amine isocyanate catalyst is used. In embodiments, the concentration of bio-based emollient is between 70-85% by weight based on the total combined weight of bio-based polyol, bio-based isocyanate, bismuth catalyst, and a bio-based emollient or mixture of bio-based emollients. In embodiments, said polyol has a molecular weight ranging from about 500-10,000. In embodiments, the number of OH units per polyol is about 2-20. In embodiments, the number of NCO units per polyol is about 2-6. In embodiments, said bio-based emollient is selected from a group of esters, hydrocarbons, carbonate, vegetable oils, or modified vegetable oils. In embodiments, said bio-based emollient has a spreading value ($mm^2$/10 min) between 500-2500. In embodiments, said bio-based emollient has an average molecular weight of 240-1200.

In some embodiments, the invention provides a process for making a polyurethane elastomer gel comprising: adding to a reaction kettle triheptanoin, coco-caprylate/caprate, dilinoleic acid/propane diol copolymer, and 1,5-pentamethylene diisocyanate based polyisocyanates; stirring the mixture at room temperature until a clear, homogeneous solution is obtained; adding bismuth neodecanoate with stirring, and heating the reaction to 60° C., at which point a colorless rubber is formed.

In further embodiments, the invention provides a process for making a polyurethane elastomer gel comprising: placing the polyurethane elastomer rubber in a drum, adding triheptanoin, milling the mixture with a Cowles mixer; running the resulting suspension through a disperser and allowing the resulting gel to cool to room temperature; and adding undecane and/or tridecane with mixing until the desired viscosity was achieved.

In embodiments, the rubber is formed without stirring at room temperature over 24 hours. In embodiments, a finisher containing an alcohol or amine may be added to quench unreacted isocyanate groups. In embodiments, said polyurethane elastomer rubber has a hardness as described herein. In embodiments, said polyurethane elastomer gel has a viscosity as described herein.

In some embodiments, the invention provides a gel composition comprising a polyurethane elastomer from the reaction of: A) castor oil; B) isophorone diisocyanate, wherein the molar ratio of isocyanate groups to hydroxyl groups is between 1:1 and 1:2; C) an optional polyurethane reaction catalyst; and D) a carrier fluid, which is cosmetically acceptable (examples of such carrier fluids include diisooctyl succinate, heptyl undecylenate, neopentyl glycol diheptanoate, coco-caprylate/caprate, triheptanoin, C13-15 alkane, squalene, undecane, tridecane), wherein solvent concentration is between 60% (w/w) and 99.9% (w/w); wherein a personal care or healthcare active ingredient may be incorporated into the polyurethane elastomer gel by dissolving it in the topically acceptable solvent during the formation of the polyurethane elastomer gel (pre-load method) or admixing it with a formed polyurethane elastomer gel (post-load method).

In embodiments, the polyurethane catalyst is a bismuth group containing catalyst. In embodiments, the carbon content of the topically acceptable solvent is >50% derived from plant sources.

In further embodiments, the invention provides a process for preparing the polyurethane elastomer gel comprising: I) reacting: A) castor oil; B) isophorone diisocyanate; and (C) an optional polyurethane reaction catalyst, in the presence of D) a topically acceptable carrier fluid. In still further embodiments, the invention provides a gel composition prepared according to the process herein.

In yet further embodiments, the invention provides a process for preparing a gel paste composition, comprising: I) shearing the polyurethane elastomer gel herein; and II) combining the sheared polyurethane elastomer gel with additional quantities of the carrier fluid to form a gel paste composition.

In yet further embodiments, the invention provides a process for preparing a gel paste composition, comprising: I) shearing the polyurethane elastomer gel herein; and II) combining the sheared polyurethane elastomer gel with an active ingredient.

BRIEF DESCRIPTION OF THE DRAWINGS

FIG. 1 shows a table describing biolastomer compatibility with common carrier fluids described in embodiments herein.

DETAILED DESCRIPTION OF THE INVENTION

Definitions

Figure 2:
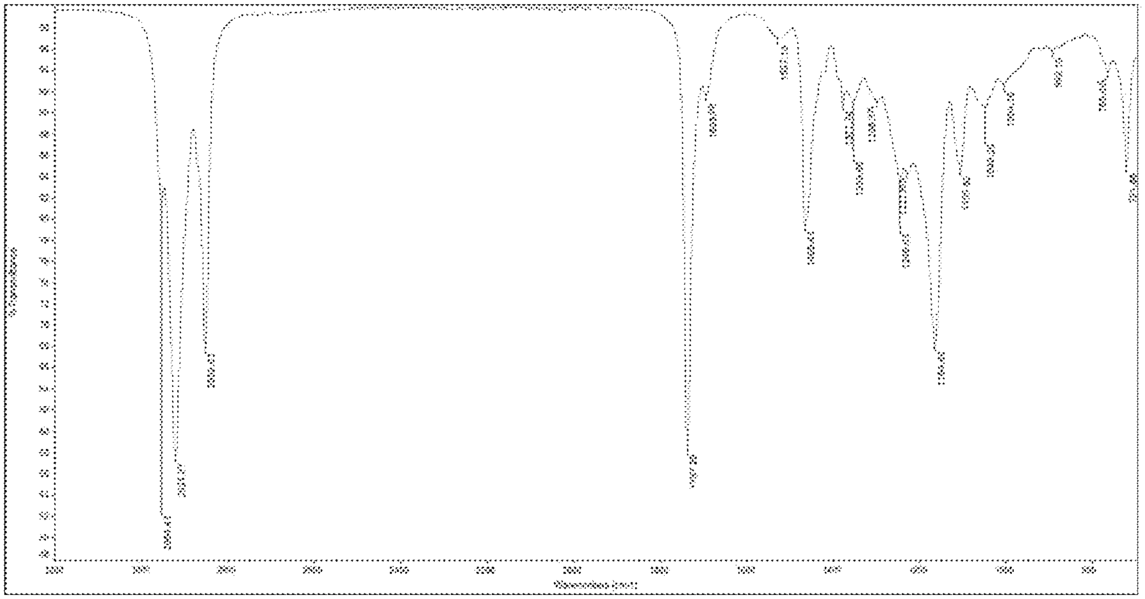
FIG. 2 shows a FTIR spectrograph of dilinoleic acid/propane diol copolymer based pentamethylene diisocyanate trimer elastomer, as described in embodiments herein.

As used herein, "a" or "an" may mean one or more. As used herein, when used in conjunction with the word "comprising," the words "a" or "an" may mean one or more than one. As used herein, "another" or "a further" may mean at least a second or more.

The term "about" as used herein means approximately ±10%. When the term "about" is used in conjunction with a numerical value or range, it modifies that value or range by extending the boundaries above and below the numerical values set forth. In general, the term "about" is used herein to modify a numerical value above and below the stated value by a variance of 10 percent, up or down (higher or lower), i.e., ±10%, unless a different variance is indicated (e.g., ±30%, ±20%, ±5%, ±1%, etc.).

The use of the term "or" in the claims is used to mean "and/or", unless explicitly indicated to refer only to alternatives or the alternatives are mutually exclusive, although the disclosure supports a definition that refers to only alternatives and "and/or."

As used herein, the terms "comprising" (and any variant or form of comprising, such as "comprise" and "comprises"), "having" (and any variant or form of having, such as "have" and "has"), "including" (and any variant or form of including, such as "includes" and "include") or "containing" (and any variant or form of containing, such as "contains" and "contain") are inclusive or open-ended and do not exclude additional, unrecited, elements or method steps. It is contemplated that any embodiment discussed in this specification can be implemented with respect to any method, and/or composition of the present disclosure.

The use of the term "for example" and its corresponding abbreviation "e.g." (whether italicized or not) means that the specific terms recited are representative examples and embodiments of the disclosure that are not intended to be limited to the specific examples referenced or cited unless explicitly stated otherwise.

As used herein, "between" is a range inclusive of the ends of the range. For example, a number between x and y explicitly includes the numbers x and y, and any numbers that fall within x and y.

As used herein the term "polyurethane" indicates materials formed by reacting a polyol with an isocyanate in the presence of an appropriate catalyst.

The term "polyol" refers to materials having functional groups containing an active hydrogen atom that can undergo a reaction with an isocyanate. Preferably, polyols contain at least two hydroxyls, amines, carboxylic acids, and/or thiol groups per molecule.

The term "polyisocyanate" refers to a substance containing two or more isocyanate functional groups.

The term "bio-based" refers to materials that mainly consist of a substance derived from living matter, also known as biomass.

The term "polyurethane elastomer rubber" refers to the reaction product of a polyol, an isocyanate, and a polyurethane catalyst in an emollient medium.

The term "polyurethane elastomer gel" refers to the product of the processed polyurethane elastomer rubber.

The present invention further relates to a polyurethane elastomer gel comprised of a bio-based polyol cross-linked with a bio-based polyisocyanate in a bio-based topically acceptable carrier fluid or mixture of bio-based topically acceptable carrier fluids. In some embodiments, the reaction is catalyzed by a topically acceptable bismuth polyurethane catalyst. The polyurethane elastomer gel described herein has good compatibility with cosmetic and natural oils and can be used as a thickener for these oils. The polyurethane elastomer gel further provides a smooth, non-tacky, non-oily, moisturizing skin feel with enhanced playtime to cosmetic formulations. The polarity of the polyurethane elastomer gel allows for its incorporation into polar cosmetic formulation mediums. Silicone elastomer gels, which are typically used in many formulations, are non-polar and are generally not compatible with polar formulation mediums, and therefore the polyurethane elastomer gels meet a critical need in the personal care industry.

By using a bio-based polyol, a bio-based polyisocyanate, and a bio-based carrier fluid, a polyurethane elastomer gel is produced comprising >99% bio-based material. Silicone elastomer gels are derived from fossil fuels which are not a renewable resource. It is generally recognized that cosmetic ingredients derived from biomass are considered to be "natural," and the market demand for natural cosmetics has fueled the industries need for a bio-based elastomer that is silicone-free.

The present invention relates to a gel composition comprising a polyurethane elastomer requiring no purification and formed in a topically acceptable solvent from the reaction of component (A), a polyisocyanate; component (B), a polyol; component (C), an optional polyurethane reaction catalyst; optionally in component (D), a topically acceptable carrier fluid.

Component (A)—Polyisocyanate

In some embodiments, component (A) has a molecular structure containing more than one isocyanate and can be produced by a number of methods from polyamines or the polymerization of polyisocyanates and should have two or more reactive isocyanate functional groups in its molecular structure. In some embodiments, the polyisocyanate comprises three isocyanate functional groups. The polyisocyanate serves as a cross-linker in the reaction, which allows the use of a bi-functional polyol copolymer to create a three-dimensional polymer network.

One preferred example of a polyisocyanate is hexamethylene diisocyanate trimer and has the following structure:

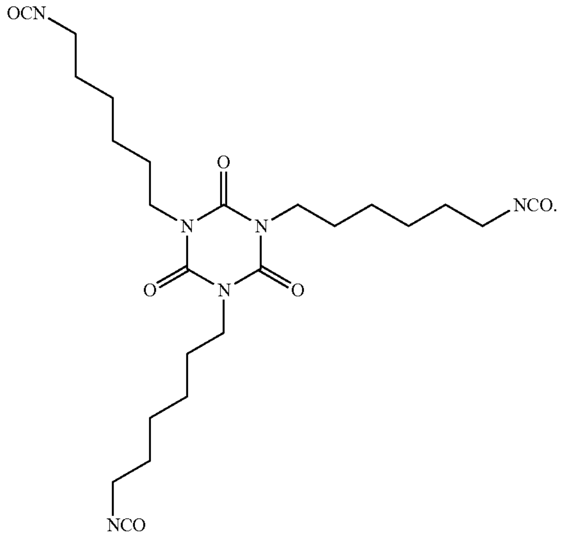

Another preferred example of a polyisocyanate is pentamethylene diisocyanate trimer and has the following structure:

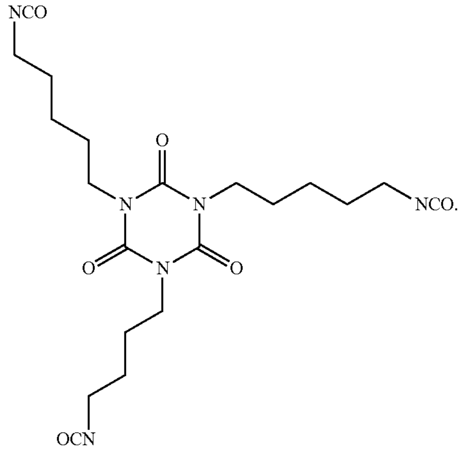

Another preferred example of a polyisocyanate is hexamethylene diisocyanate and has the following structure:

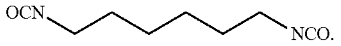

Another preferred example of a polyisocyanate is pentamethylene diisocyanate and has the following structure:

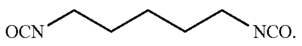

Another preferred example of a polyisocyanate is isophorone diisocyanate and has the following structure:

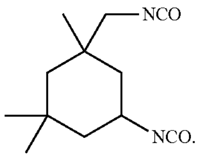

Another preferred example of a polyisocyanate is 4,4'-methylenebis(phenyl isocyanate) and has the following structure:

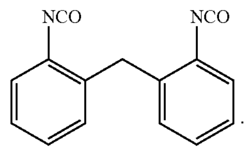

Another preferred example of a polyisocyanate is toluene diisocyanate and has the following structure:

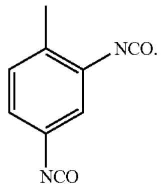

Another preferred example of a polyisocyanate is hexamethylene diisocyanate biuret.

Further non-limiting examples of polyisocyanates containing two isocyanate groups include bis(Isocyanatomethyl)benzene; 1,3-bis(Isocyanatomethyl)cyclohexane; Diphenylmethane diisocyanate; Hexamethylenediisocyanate; Hexamethylenediisocyanate based polyisocyanates; 1,5-pentamethylene diisocyanate; Isocyanato methylethylbenzene; Isophorone diisocyanate; Methylene bis-(4-cyclohexylisocyanate); M-Tetramethylene diisocyanate; meta-Tetramethylenexylenediisocyanate; Saturated methylene diphenyldiisocyanate; and Toluene diisocyanate.

Component (B)—Polyol

In some embodiments, component (B) has a molecular structure containing more than one hydroxyl group that can undergo a reaction with an isocyanate. In certain embodiments, component (B) contains nucleophilic groups other than hydroxyl and the term "polyol" refers to materials having a reactive hydrogen that can react with isocyanates. Preferably, polyols contain at least two hydroxyls, amines, carboxylic acids, and/or thiol groups per molecule.

When polyols containing three or more functional groups are used, a di-functional isocyanate (e.g., containing two isocyanate functional groups) may be used for synthesis of polyurethane elastomer gels. Exemplary di-functional isocyanates are provided herein and include bis(Isocyanatomethyl)benzene; 1,3-bis(Isocyanatomethyl)cyclohexane; Diphenylmethane diisocyanate; Hexamethylenediisocyanate; Hexamethylenediisocyanate based polyisocyanates; 1,5-pentamethylene diisocyanate; Isocyanato methylethylbenzene; Isophorone diisocyanate; Methylene bis-(4-cyclohexylisocyanate); M-Tetramethylene diisocyanate; meta-Tetramethylenexylenediisocyanate; Saturated methylene diphenyldiisocyanate; Toluene diisocyanate.

One preferred example of a polyol is castor oil, which naturally contains multiple hydroxyl groups and is bio-based. The molecular structure of natural castor oil is a triglyceride with three pendant carbon chains. Generally, each carbon has a double bond at the 9,10 position and a hydroxyl group on the $12^{th}$ carbon. Castor oil in nature has a hydroxyl value of approximately 160-165 with a fatty acid distribution of approximately 89% $C_{18}OH$ and 9% $C_{18}$. Thus, not all of the carbon chain lengths in natural or untreated castor oil contain an OH group, and on average, only about 90% of said chains contain an OH group. The principal component of castor oil is ricinolein and has the following structure:

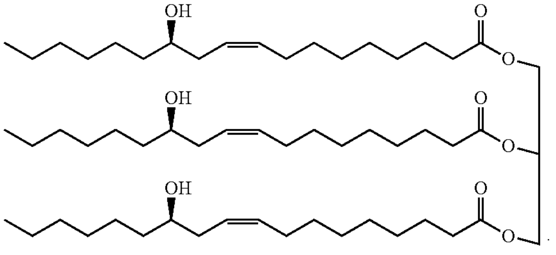 [SMILES: CCCCCC[C@@H](O)C/C=C\CCCCCCCC(=O)OCC(COC(=O)CCCCCCC/C=C\C[C@H](O)CCCCCC)OC(=O)CCCCCCC/C=C\C[C@H](O)CCCCCC]

Another preferred example of a polyol is dilinoleic acid/dilinoleic diol copolymer, and is reported to have the following structure:

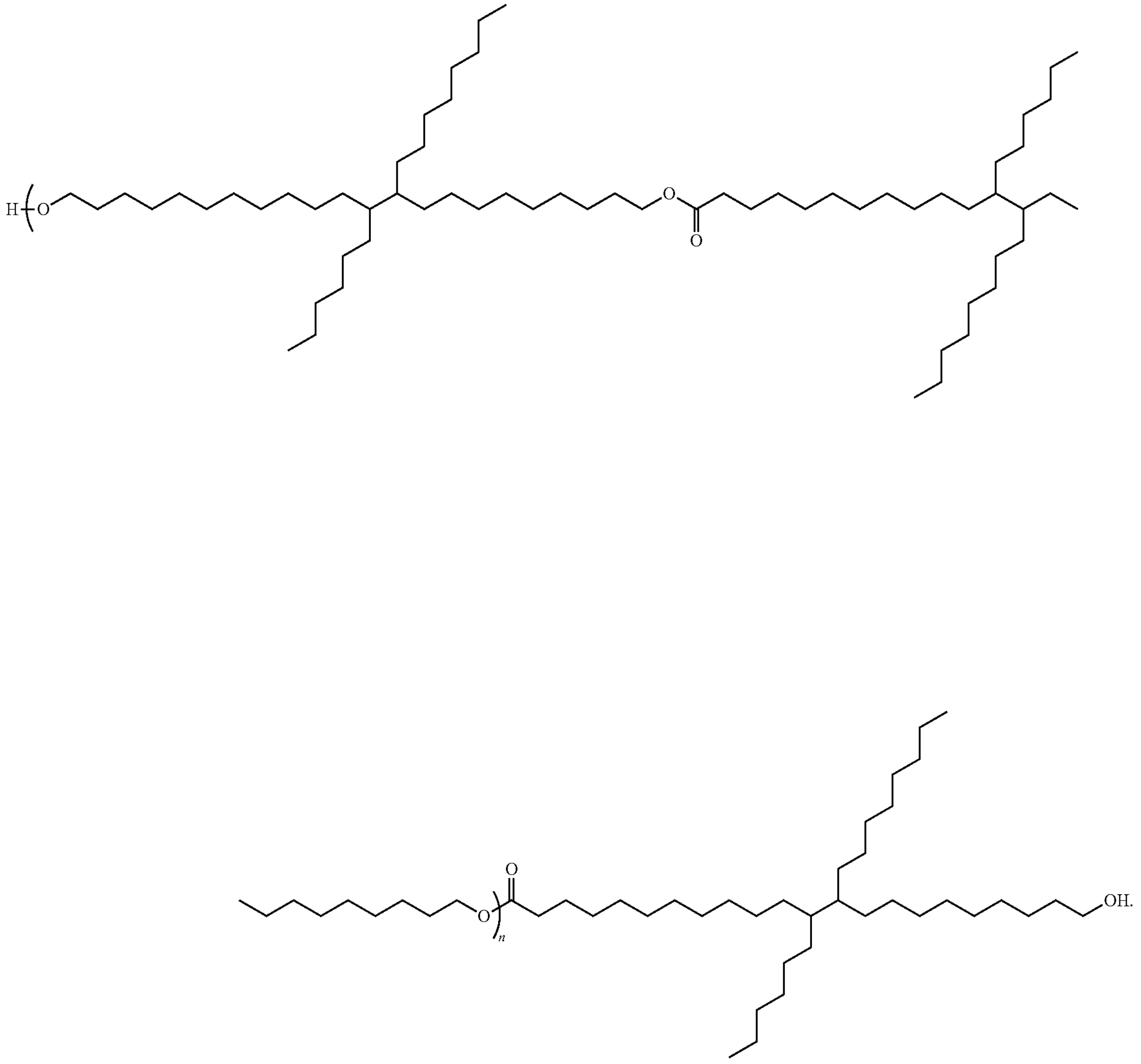

Another preferred example of a polyol is dilinoleic acid/propane diol copolymer (also called "dilinoleic acid/propane diol copolymer"), and is reported to have the following structure:

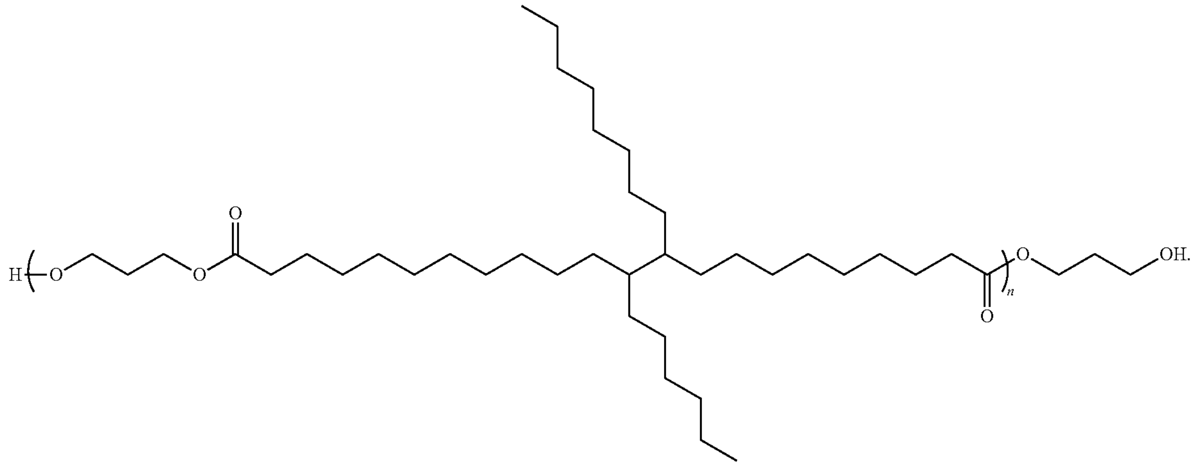

Dilinoleic acid/propane diol copolymer is 100% bio-based, has film forming properties, is non-tacky, and has good compatibility with cosmetic and natural oils. Preferably, the dilinoleic acid/propane diol copolymer should be terminated in hydroxy groups and have a low acid value, as hydroxyl groups react more readily with isocyanates than carboxylic acids. The molecular weight of the dilinoleic acid/propane diol copolymer can be between 500-10000 g/mol, and preferably between 1000-3000 g/mol. Castor oil polyurethane elastomer gels and dilinoleic acid/propane diol polyurethane elastomer gels demonstrate similar properties.

Another preferred example of a polyol is dilinoleic diol, and is reported to have the following structure:

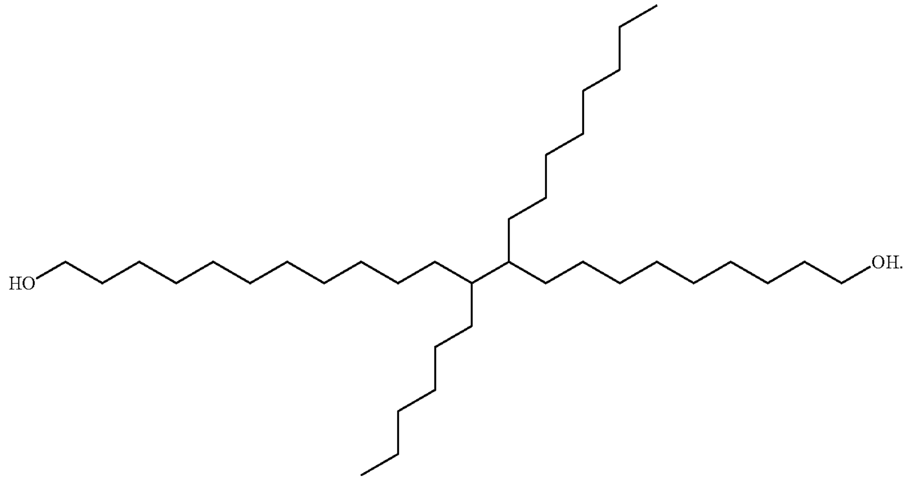 [SMILES: CCCCCCCCC(CCCCCCCCCO)C(CCCCCC)CCCCCCCCCCCO]

Another preferred example of a polyol is dilinoleic diamine, and is reported to have the following structure:

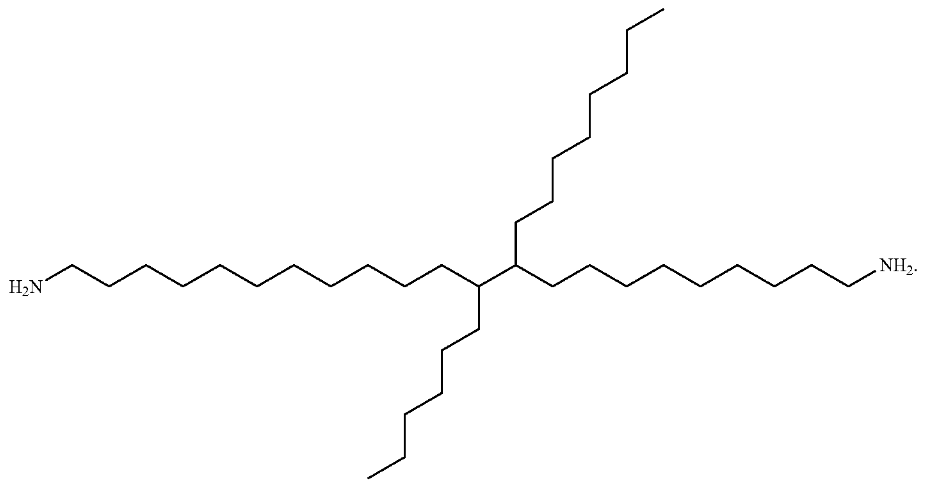 [SMILES: CCCCCCCCC(CCCCCCCCCN)C(CCCCCC)CCCCCCCCCCCN]

Another preferred example of a polyol is hexamethylene diamine, and has the following structure:

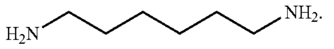

Other appropriate polyols include glycerol, polyglycerol, pentaerythritol, pentaerythritol tetrakis(3-mercaptopropionate), trimethylol propane, mercaptanized soybean oil, glycerol propoxylate, glyceryl poly(oxypropylene) triamine, and melamine.

Further exemplary polyols include, but are not limited to, Dilinoleic acid/propanediol copolymer; Propylene glycol/azelaic acid copolymer; Azelate Polyol; Propylene glycol/sebacic acid copolymer; 1,3-Propane diol/azelaic acid copolymer; 1,3-Propane diol/sebacic acid copolymer; 1,3-Butane diol/azelaic acid copolymer; 1,3-Butane diol/sebacic acid copolymer; 1,4-Butane diol/azelaic acid copolymer; 1,4-Butane diol/sebacic acid copolymer; Propylene glycol/apidic acid copolymer; 1,3-Propane diol/apidic acid copolymer; 1,3-Butane diol/apidic acid copolymer; 1,4-Butane diol/apidic acid copolymer; Capryloyl Glycerin/sebacic acid copolymer; Trimethylpentanediol/apidic acid copolymer; Capryloyl glycerin/sebacic acid copolymer; Diheptyl succinate (and) capryloyl glycerin/sebacic acid copolymer;

Polyhydroxystearic acid; Polyether; Polybutylene succinate; Polylactic acid; Polyethylene terephthalate; Polyester; Polydimethylsiloxane, hydroxy terminated; Polyethylene Glycol; Polyoxazoline; Polyglycerol; Polystyrenes; Polyhydroxyalkanoates; Polysaccharides; Polylactides; Polyethylene; Starch; Cellulose; Chitin; Chitosan; Pullulan; Collagen; Gelatin; Lignin; Polysaccharides; Alginate; Polyethylene terephthalate; Polytrimethylene terephthalate; Poly(ethylene 2,5-furandicarboxylate); Polyamides; Polyterpenes; Polyethylene 2,5-furandicarboxylate; Polycaprolactone; Polytetrahydrofuran; Polylactides; Polyglycolides; Polydioxanones; Polycarbonates; Polylactide-co-glycolides; Polyanhydrides; Polyphosphazenes; Polyphophoesters; Glycerol; Castor Oil; Jatropha Oil; Multi-hydroxy soybean oil; Palm oil; Hydrogenated Castor Oil; Caprylyl glycol; Glyceryl caprylate; Ethylhexylglycerin; 1,2-hexanediol; Hexylene glycol; Glyceryl undecylenate; Methylpropanediol; 1,2-hexanediol; Pentaerythritol; Dipentaerythritol; Tripentaerythritol; Trimethyoyl propane; Isosorbide; Ethylene glycol; Diethylene glycol; Triethylene glycol; Tetraethylene glycol; Propylene glycol; Dipropylene glycol; Tripropylene glycol; 1,3-Butanediol; 1,4-Butanediol; Neopentyl glycol; 1,6-hexanediol; 1,4-Cyclohexanedimethanol; Ethanolamine; Diethanolamine; Methyldiethanolamine; Phenyldiethanolamine; 1,2,6-Hexanetriol; Triethanolamine; Diethyltoluenediamine; Dimethylthiotoluenediane; Citric acid; Lactic acid; Polylactic acid; Dilinoleic acid; Trilinoleic acid; Azelaic acid; and Sebacic acid.

Component (C)—Polyurethane Reaction Catalyst:

In some embodiments, component (C), the polyurethane reaction catalyst, is optionally used to increase the rate of polyurethane elastomer formation. Bismuth carboxylates are the preferred catalysts for the synthesis of the polyurethane elastomer gel due to their favorable toxicity profile and acceptable use in topical products.

Preferably, bismuth neodecanoate is used as the polyurethane catalyst. Zinc, tin, and amine based polyurethane catalysts can also be used. Appropriate polyurethane catalysts include but are not limited to: Triethylenediamine, N,N,N',N",N"-Pentamethyldiethylenetriamine, 1,2-Dimethylimidazole, N,N,N',N'-Tetramethyl-1,6-hexanediamine, N,N',N'-Trimethylaminoethylpiperazine, 1,1'-[[3-(dimethylamino)propyl]imino]bispropan-2-ol, N,N,N'-Trimethylaminoethylethanolamine, N,N',N"-Tris(3-dimethylaminopropyl)-hexahydro-s-triazine, 1,4-diazabicyclo[2.2.2]octane, Stannous octoate, Stannous oxalate, Stannous oxide, Stannous chloride, Dioctyltin di(2-hexylhexanoate)-solution, Dioctyltin dithioglycolate, Dioctyltin dilaurate, Dioctyltin oxide blend, Dibutyltin dilaurate, Monobutyl tin tris-(2-ethylhexanoate), Dioctyltin diketanoate, Dioctyltin diacetate, Dioctyltin oxide, Dibutyltin diacetate, Modified dibutyltin diacetate, Dibutyltin oxide, Monobutyltin dihydroxychloride, Organotin oxide, Monobutyltin oxide, Dioctyltin dicarboxylate, Dioctyltin carboxylate, Dioctyltin stannoxane, Zinc neodecanoate, Zinc octoate, Zinc acetylacetonate, Zinc oxalate, Zinc acetate, Bismuth carboxylates, and Zinc neodecanoate.

Component (D)—Carrier Fluid

In some embodiments, the polyurethane elastomer is contained in an optional carrier fluid (D) that is topically acceptable. In exemplary embodiments, the carrier fluid is a "topically acceptable carrier fluid" which is a solvent for topical use on cutaneous surfaces i.e. skin, lips, mucous membranes, etc. The terms "topically acceptable" and "cosmetically acceptable" can be used interchangeably herein, and the topically acceptable carrier fluid can also be referred to herein as an "emollient." Although it is not required, typically the carrier fluid may be the same as the solvent used for conducting the polyurethane elastomer reaction as described above. The topically acceptable carrier fluid used for the synthesis of the polyurethane elastomer rubber and gel can be fully, partially, or not bio-based. As described herein, "bio-based" refers to materials that mainly consist of a substance/s derived from living matter, also known as biomass.

The topically acceptable carrier fluid should be compatible with the reaction to form the polyurethane elastomer rubber described herein, such that the rubber is not too hard and/or brittle to process into a gel. When processing the polyurethane elastomer rubber into a gel, a carrier fluid with the appropriate polarity should be used in order to swell the elastomer granules while milling. If the emollient is not able to swell the granules, the polyurethane elastomer rubber cannot be processed into a smooth gel. Triglycerides, esters, and ethers with appropriate polarity can be used to swell the elastomer granules during the milling process. In some embodiments, the topically acceptable carrier fluid comprises a triglyceride, ester, alkane, ether, or a mixture thereof. Preferably, the topically acceptable carrier fluid is triheptanoin or a mixture of triheptanoin and coco-caprylate/caprate. Triheptanoin is a preferred carrier fluid for swelling the elastomers granules as described herein. Triheptanoin has relatively high polarity, is 100% bio-based, and has a low viscosity and a light non-oily skin feel.

Once the polyurethane elastomer rubber is processed into a smooth gel, volatile carrier fluids with a dry skin feel can be added to the gel with high sheer mixing until the desired viscosity is achieved. Volatile carrier fluids serve to enhance the dry feeling of polyurethane elastomer gels on the skin. Triglycerides, esters, ethers, and alkanes can be used during this process. Preferably, undecane and/or tridecane and/or coconut alkanes are used.

The stability of the polyurethane elastomer gel is partially dependent on the carrier fluid or mixture of carrier fluids used in the synthesis of the polyurethane elastomer rubber and gel. If the polarity of the carrier fluid is too low, the gel may initially form but will separate over time. Generally, triglycerides, esters, ethers, and alkanes can be used in various combinations. Preferably, a mixture of triheptanoin, coco-caprylate/caprate, and undecane and/or tridecane in a ratio of about 1/1/0.5 is used. Surfactants may also be used to maintain gel stability if separation occurs.

The topically acceptable carrier fluids preferably have a viscosity between 1-65 mPas at 20° C. The spreading value of the topically acceptable carrier fluid is preferably between 500-2500 $mm^2$/10 min. Appropriate topically acceptable carrier fluids for the synthesis of the polyurethane elastomer rubber and processing of the polyurethane elastomer gel include but are not limited to: Bis-Diglyceryl Polyacyladipate-1, Bis-Diglyceryl Polyacyladipate-1, Bis-Diglyceryl Polyacyladipate-2, Butylene Glycol Dicaprylate/Dicaprate, Butyrospermum Parkii Butter, Caprylic/Capric Glycerides, Caprylic/Capric Triglyceride, Caprylic/Capric/Myristic/Stearic Triglyceride, Caprylic/Capric/Succinic Triglyceride, Caprylyl Methicone, Coco-Caprylate/Caprate, Decamethylcyclopentasiloxane, Decyl Oleate, Dimethiconol, Diphenylsilanediol, Dodecamethylcyclohexasiloxane, Ethyl trisiloxane, Glyceryl Caprylate, Glyceryl Caprylate, Glyceryl Citrate/Lactate/Linoleate/Oleate, Glyceryl Citrate/Lactate/Linoleate/Oleate, Glyceryl Cocoate, Glyceryl Isostearate, Glyceryl Oleate, Glyceryl Ricinoleate, Glyceryl Ricinoleate, Tocopherol, Glyceryl Stearate, Glyceryl Stearate, Glyceryl Stearate Citrate, Hexamethyldisilazane, Hexamethyldisiloxane, Hydrogenated Coco-Glycerides, Hydrogenated Palm Oil, Hydroxytrimethylsilane, Isopropoxytrimethylsilane, Methylheptyl Isostearate, Octamethylcyclotetrasiloxane, Oleyl Erucate, Olus Oil, Organo-modified Siloxanes, Organosilicone Fluids, PCA Glyceryl Oleate, PEG-6 Caprylic/Capric Glycerides, Phenyltrichlorosilane, Poly(dimethyl siloxane), Poly(ethylene glycol)-containing siloxanes, Polydimethylsiloxane, Polyglyceryl-2 Caprate, Polyglyceryl-3 Caprate, Polyglyceryl-3 Caprate, Polyglyceryl-3 Diisostearate, Polyglyceryl-3 Polyricinoleate, Polyglyceryl-4 Cocoate, Polyglyceryl-4 Cocoate, Propylene Carbonate, Propylene Carbonate, Propylene Carbonate, Propylene Carbonate, Propylene Glycol Dicaprylate/Dicaprate, Propylene Glycol Dicaprylate/Dicaprate, Propylene Glycol Dicaprylate/Dicaprate, Silicone oil, Stearalkonium Bentonite, Stearalkonium Hectorite, Stearalkonium Hectorite, Stearalkonium Hectorite, Triheptanoin, Trimethyl(bromodifluoromethyOsilane, Trimyristin, and Tristearin.

In some embodiments, the topically acceptable carrier fluid is at a concentration of about 0% to about 99.9% (w/w) of the gel composition, about 1% (w/w) to about 99.9% (w/w) of the gel composition, about 10% (w/w) to about 99.9% (w/w) of the gel composition, about 20% (w/w) to about 99.9% (w/w) of the gel composition, about 30% (w/w) to about 99.9% (w/w) of the gel composition, about 40% (w/w) to about 99.9% (w/w) of the gel composition, about 50% (w/w) to about 99.9% (w/w) of the gel composition, about 60% (w/w) to about 99.9% (w/w) of the gel composition, about 70% (w/w) to about 99.9% (w/w) of the gel composition, about 80% (w/w) to about 99.9% (w/w) of the gel composition, or about 90% (w/w) to about 99.9% (w/w) of the gel composition. In certain embodiments, the gel composition does not comprise a topically acceptable carrier fluid. In some embodiments, a process for preparing the gel composition herein is conducted in the presence of a topically acceptable carrier fluid. In further embodiments, a process for preparing the gel composition herein is not conducted in the presence of a topically acceptable carrier fluid.

Component (E)—Active Ingredient

In some embodiments, the gel compositions herein further comprise component (E), an active ingredient.

In some embodiments, component (E) is a "pharmaceutically active ingredient" selected from any personal or health care active ingredient. As used herein, a "pharmaceutically active ingredient" means any compound or mixtures of compounds that are known in the art as additives in the personal care formulations that are typically added for the purpose of treating skin, lips or to provide a cosmetic and/or aesthetic benefit. A "healthcare active ingredient" means any compound or mixtures of compounds that are known in the art to provide a pharmaceutical or medical benefit. Thus, "healthcare active ingredient" includes materials considered an active ingredient or active drug ingredient as generally used and defined by the United States Department of Health & Human Services Food and Drug Administration, contained in Title 21, Chapter I, of the Code of Federal Regulations, Parts 200-299 and Parts 300-499. Thus, active ingredient can include any component that is intended to furnish pharmacological activity or other direct effect in the diagnosis, cure, mitigation, treatment, or prevention of disease, or to affect the structure or any function of the body of a human or other animals. The phrase can include those components that may undergo chemical change in the manufacture of drug products and be present in drug products in a modified form intended to furnish the specified activity or effect.

Some representative examples of active ingredients include: drugs, vitamins, minerals, hormones, topical antimicrobial agents such as antibiotic active ingredients, antifungal active ingredients for the treatment of athlete's foot, jock itch, or ringworm, and acne active ingredients, astringent active ingredients, deodorant active ingredients, wart remover active ingredients, corn and callus remover active ingredients, pediculicide active ingredients for the treatment of head, pubic (crab) and body lice, active ingredients for the control of dandruff, seborrheic dermatitis, or psoriasis, and sunburn prevention and treatment agents.

Useful active ingredients for use in processes according to the invention include Vitamins and its derivatives, including "pro-vitamins." Vitamins useful herein include, but are not limited to, Vitamin A, retinol, C—C esters of retinol, Vitamin E, tocopherol, esters of vitamin E, and mixtures thereof. Retinol includes trans-retinol, 1.3-cis-retinol, 11-cis-retinol, 9-cis-retinol, and 3,4-didehydro-retinol, Vitamin C and its derivatives, Vitamin B, Vitamin B. Pro Vitamin B5, panthenol, Vitamin B, Vitamin B2, niacin, folic acid, biotin, and pantothenic acid. Other suitable vitamins and the INCI names for the vitamins considered included herein are ascorbyl dipalmitate, ascorbyl methylsilanol pectinate, ascorbyl palmitate, ascorbyl Stearate, ascorbyl glucoside, sodium ascorbyl phosphate, sodium ascorbate, disodium ascorbyl sulfate, potassium (ascorbyl/tocopheryl)phosphate.

Retinol, it should be noted, is an International Nomenclature Cosmetic Ingredient Name (INCI) designated by The Cosmetic, Toiletry, and Fragrance Association (CTFA), Washington D.C., for vitamin A. Other suitable vitamins and the INCI names for the vitamins considered included herein are retinylacetate, retinyl palmitate, retinyl propionate, o-tocopherol, tocophersolan, tocopheryl acetate, tocopheryl linoleate, tocopheryl nicotinate, and tocopheryl succinate.

The pharmaceutically active ingredient used in processes according to the invention can be an active drug ingredient. Representative examples of some suitable active drug ingredients which can be used are hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, Vincristine, bleomycin sulfate, aurothioglucose, suramin, mebendazole; clonidine, scopolamine, propranolol, phenylpropanolamine hydrochloride, ouabain, atropine, haloperidol, isosorbide, nitroglycerin, ibuprofen, ubiquinones, indomethacin, prostaglandins, naproxen, Salbutamol, guanaben Z, labetalol, pheniramine, metrifonate, and steroids.

Considered to be included herein as active drug ingredients for purposes of the present invention are antiacne agents such as benzoyl peroxide and tretinoin; antibacterial agents such as chlorohexadiene gluconate; antifungal agents such as miconazole nitrate; anti-inflammatory agents; corticosteroidal drugs; non-steroidal anti-inflammatory agents such as diclofenac; antipsoriasis agents such as clobetasol propionate; anesthetic agents such as lidocaine; antipruritic agents; antidermatitis agents; and agents generally considered barrier films.

The pharmaceutically active ingredient E) of the present invention can be a protein, such as an enzyme. The internal inclusion of enzymes in the polyurethane elastomer gel have advantages to prevent enzymes from deactivating and maintain bioactive effects of enzymes for a longer time. Enzymes include, but are not limited to, commercially available types, improved types, recombinant types, wild types, variants not found in nature, and mixtures thereof. For example, suitable enzymes include hydrolases, cutinases, oxidases, transferases, reductases, hemicellulases, esterases, isomerases, pectinases, lactases, peroxidases, laccases, catalases, and mixtures thereof. Hydrolases include, but are not limited to, proteases (bacterial, fungal, acid, neutral or alkaline), amylases (alpha orbeta), lipases, mannanases, cellulases, collagenases, lisozymes, superoxide dismutase, catalase, and mixtures thereof. Said proteases include, but are not limited to, trypsin, chymotrypsin, pepsin, pancreatin and other mammalian enzymes; papain, bromelain and other botanical enzymes; subtilisin, epidermin, nisin, naringinase(L-rhammnosidase) urokinase and other bacterial enzymes. Said lipases include, but are not limited to, triacyl-glycerol lipases, monoacyl glycerol lipases, lipoprotein lipases, e.g. steapsin, erepsin, pepsin, other mammalian, botanical, bacterial lipases and purified ones. Natural papain is preferred as said enzyme. Further, stimulating hormones, e.g. insulin, can be used together with these enzymes to boost the effectiveness of them.

The pharmaceutically active ingredient may also be a sunscreen agent. The Sunscreen agent can be selected from any Sunscreen agent known in the art to protect skin from the harmful effects of exposure to sunlight. The sunscreen compound is typically chosen from an organic compound, an inorganic compound, or mixtures thereof that absorbs ultraviolet (UV) light. Thus, representative non limiting examples that can be used as the sunscreen agent include; aminobenzoic acid, cinoxate, diethanolamine methoxycinnamate, digalloyl trioleate, dioxybenzone, ethyl 4-bis(Hydroxypropyl) aminobenzoate, glyceryl aminobenzoate, homosalate, lawsone with dihydroxyacetone, menthyl anthranilate, octocrylene, octyl methoxycinnamate, octyl salicylate, oxybenzone, padimate 0, phenylbenzimidazole sulfonic acid, red petrolatum, sulisobenzone, titanium dioxide, trolamine salicylate, cetarninosalol, allatoin, PABA, benzalphthalide, benzophenone, benzophenone 1-12, 3-benzylidene camphor, benzylidenecamphor hydrolyzed collagen sulfonamide, benzylidene camphor sulfonic acid, benzyl salicylate, bomelone, bumetriozole, butyl methoxydibenzoylmethane, butyl PABA, ceria/silica, ceria/silica talc, cinoxate, DEA-methoxycinnamate, dibenzoxazol naphthalene, di-t-butyl hydroxybenzylidene camphor, digalloyl trioleate, diisopropyl methyl cinnamate, dimethyl PABA ethyl cetearyldimonium tosylate, dioctyl butamido triazone, diphenyl carbomethoxy acetoxy naphthopyran, disodium bisethylphenyl tiamminotriazine stilbenedisulfonate, disodium sistyrylbiphenyl triaminotriazine stilbenedisulfonate, disodium distyrylbi phenyl disulfonate, drometrizole, drometrizole trisiloxane, ethyl dihydroxypropyl PABA, ethyl diisopropylcinnamate, ethyl methoxycinnamate, ethyl PABA, ethyl urocanate, etrocrylene ferulic acid, glyceryl octanoate dimethoxycinnamate, glyceryl PABA, glycol salicylate, homosalate, isoamyl p-methoxycinnamate, isopropylbenzyl salicylate, isopropyl dibenzolylmethane, isopropyl methoxycinnamate, menthyl anthranilate, menthyl salicylate, 4-methylbenzylidene, camphor, octocrylene, octrizole, octyl dimethyl PABA, octyl methoxycinnamate, octyl salicylate, octyl triazone, PABA, PEG-25 PABA, pentyl dimethyl, PABA, phenylbenzimidazole sulfonic acid, polyacrylamidomethyl benzylidene camphor, potassium methoxycinnamate, potassium phenylbenzimidazole sulfonate, red petrolatum, sodium phenylbenzimidazole sulfonate, sodium urocanate, TEA-phenylbenzimidazole sulfonate, TEA-salicylate, terephthalylidene dicamphor sulfonic acid, titanium dioxide, zinc dioxide, serium dioxide, TriPABA panthenol, urocanic acid, and VA/crotonates/methacryloxybenzophenone-1 copolymer.

The sunscreen agent can be a single one or combination of more than one. Alternatively, the sunscreen agent is a cinnamate based organic compound, or alternatively, the sunscreen agent is octyl methoxycinnamate, such as Uvinul R. MC 80 (an ester of para-methoxycinnamic acid and 2-ethyl hexanol).

Component (E) may also be a fragrance or perfume. The perfume can be any perfume or fragrance active ingredient commonly used in the perfume industry. These compositions typically belong to a variety of chemical classes, as varied as alcohols, aldehydes, ketones, esters, ethers, acetates, nitrites, terpenic hydrocarbons, heterocyclic nitrogen or sulfur containing compounds, as well as essential oils of natural or synthetic origin. Many of these perfume ingredients are described in detail in standard textbook references such as Perfume and Flavour Chemicals, 1969, S. Arctander, Montclair, N.J.

Fragrances may be exemplified by, but not limited to, perfume ketones and perfume aldehydes. Illustrative of the perfume ketones are buccoxime, isojasmone, methyl beta naphthyl ketone, musk indanone, tonalid/musk plus, Alpha Damascone, Beta-Damascone, Delta-Damascone, Iso Damascone, Damascenone, Damarose, Methyl Dihydrojasmonate, Menthone, Carvone, Camphor, Fenchone, Alpha-lonone, Beta-lonone, Gamma-Methyl So called lonone, Fleuramone, Dihydrojasmone, Cis-Jasmone, Iso-E-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or LiveScone, 6-Isopropyldecahydro-2-naphtone, Dimethyl-Octenone, Freskomenthe, 4-(1-Ethoxyvinyl)-3,3,5,5-tetramethyl-Cyclohexanone, Methyl-Heptenone, 2-(2-(4-Methyl-3-cyclohexen-1-yl)propyl)-cyclopentanone, 1-(p-Menthen-6(2)-yl)-1-propanone, 4-(4-Hydroxy-3-methoxyphenyl)-2-butanone, 2-Acetyl-3,3-Dimethyl Norbornane, 6,7-Dihydro-1,1,2,3,3-Pentamethyl-4(5H)-Indanone, 4-Damascol, Dulcinyl or Cassione, Gelsone, Hexylon, Isocyclemone E. Methyl Cyclocitrone, Methyl Lavender-Ketone, Orivon, Para-tertiary-Butyl-Cyclohexanone, Verdone, Delphone, Muscone, Neobutenone, Plica tone, Veloutone, 2,4,4,7-Tetramethyl-oct-6-en-3-one, and Tetrameran.

More preferably, the perfume ketones are selected for its odor character from Alpha Damascone, Delta Damascone, Iso Damascone, Carvone, Gamma-Methyl-lonone, Iso-E-Super, 2.4.4.7-Tetramethyl-oct-6-en-3-one, Benzyl Acetone, Beta Damascone, Damascenone, methyl dihydrojasmonate, methyl cedrylone, and mixtures thereof.

Preferably, the perfume aldehyde is selected for its odor character from adoxal, anisic aldehyde, cymal, ethylvanillin, florhydral, helional, heliotropin, hydroxycitronellal, koavone, lauric aldehyde, lyral, methyl nonyl acetaldehyde, P. T. bucinal, phenyl acetaldehyde, undecylenic aldehyde, vanillin, 2,6,10-trimethyl-9-undecenal, 3-dodecen-1-al, alpha-n-amyl cinnamic aldehyde, 4-methoxybenzaldehyde, benzaldehyde, 3-(4-tert-butylphenyl)-propanal, 2-methyl-3-(para-methoxyphenyl propanal, 2-methyl-4-(2,6,6-trim ethyl-2(1)-cyclohexen-1-yl) butanal, 3-phenyl-2-propenal, cis-/trans-3,7-dimethyl-2,6-octadien-1-al, 3,7-dimethyl-6-octen-1-al. (3,7-dimethyl-6-octenyl)oxyacetaldehyde, 4-isopropylbenzyaldehyde, 1,2,3,4,5,6,7,8-octahydro-8.8-dimethyl-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptenal, 4-(tri cyclo[5.2.1.0(2,6)-decylidene-8)-butanal, octahydro-4,7-methano-1H-indenecarboxaldehyde, 3-ethoxy-4-hydroxy benzaldehyde, para-ethyl-alpha,alpha-dimethyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, undecenal, 2,4,6-trimethyl-3-cyclohexene-1-carboxaldehyde, 4-(3)(4-methyl-3-pentenyl)-3-cyclohexen-carboxaldehyde, 1-dodecanal, 2,4-dimethyl cyclohexene-3-carboxaldehyde, 4-(4-hydroxy-4-methylpentyl)-3-cylohexene 1-carboxaldehyde, 7-methoxy-3,7-dimethyloctan-1-al, 2-methyl undecanal, 2-methyl decanal, 1-nonanal, 1-octanal, 2,6,10-trimethyl-5.9-undecadienal, 2-methyl-3-(4-tertbutyl)propanal, dihydrocinnamic aldehyde, 1-methyl-4-(4-methyl 3-pentenyl)-3-cyclohexene-1-carboxaldehyde, 5(or 6)-methoxy hexahydro-4,7-methanoindan-1(or 2)-carboxaldehyde, 3,7-dimethyloctan-1-al, 1-undecanal, 10-undecen-1-al, 4-hydroxy-3-methoxybenzaldehyde, 1-methyl-3-(4-methylpentyl)-3-cyclhexenecarboxaldehyde, 7-hydroxy-3,7-dimethyloctanal, trans-4-decenal, 2,6-nonadienal, paratolylacetaldehyde, 4-methylphenylacetaldehyde, 2-methyl-4-(2,6,6-trimethyl-1-cyclohexen-1-yl)-2-butenal, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5.9-undecadien-1-al), hexahydro-4,7-methanoindan-1-carboxaldehyde, 2-methyloctanal, alpha-methyl-4-(1-methylethyl)benzene acetaldehyde, 6,6-dimethyl-2-norpinene-2-propionaldehyde, para methyl phenoxyacetaldehyde, 2-methyl-3-phenyl-2-propen-1-al, 3.5.5-trimethylhexanal, Hexahydro-8,8-dimethyl-2-naphthaldehyde, 3-propyl-bicyclo[2.2.1-hept-5-ene-2-carbaldehyde, 9-decenal, 3-methyl-5-phenyl-1-pentanal, methylnonyl acetaldehyde, hexanal, trans-2-hexenal, 1-p-menthene-q-carboxaldehyde and mixtures thereof. More preferred aldehydes are selected for their odor character from 1-decanal, benzaldehyde, florhydral, 2,4-dimethyl-3-cyclohexen-1-carboxaldehyde, cis/trans-3,7-dimethyl-2,6-octadien-1-al, heliotropin, 2,4,6-trimethyl-3-cyclohexene-1-carboxaldehyde, 2,6-nonadienal, alpha-amyl-cinnamic aldehyde, alpha-n-hexyl-cinnamic aldehyde, P. T. Bucinal, lyral, cymal, methylnonyl acetaldehyde, hexanal, trans-2-hexenal, and mixture thereof. In the above list of perfume ingredients, some are commercial names conventionally known to one skilled in the art, and also includes isomers. Such isomers are also suitable for use in the present invention.

Component (E) may also be one or more plant extracts. Examples of these components are as follows: Ashitaba extract, avocado extract, hydrangea extract, Althea extract, Arnica extract, aloe extract, apricot extract, apricot kernel extract, Ginkgo Biloba extract, fennel extract, turmeric Curcuma extract, oolong tea extract, rose fruit extract, Echinacea extract, Scutellaria root extract, Phellodendro bark extract, Japanese Coptis extract, Barley extract, Hyperium extract, White Nettle extract, Watercress extract, Orange extract, Dehydrated saltwater, seaweed extract, hydrolyzed elastin, hydrolyzed wheat powder, hydrolyzed silk, Chamomile extract, Carrot extract, Artemisia extract, Glycyrrhiza extract, hibiscustea extract, Pyracantha Fortuneana Fruit extract, Kiwi extract, Cinchona extract, cucumber extract, guanocine, Gardenia extract, Sasa Albo-marginata extract, Sophora root extract, Walnut extract, Grapefruit extract, Clematis extract, Chlorella extract, mulberry extract, Gentiana extract, black tea extract, yeast extract, burdock extract, rice bran ferment extract, rice germ oil, comfrey extract, collagen, cowberry extract, Gardenia extract, Asiasarum Root extract, Family of Bupleurum extract, umbilical cord extract, Salvia extract, Saponaria extract, Bamboo extract, Crataegus fruit extract, Zanthoxylum fruit extract, Shiitake extract, Rehmannia root extract, gromwell extract, Perilla extract, linden extract, Filipendula extract, peony extract, calamus root extract, white birch extract, Horsetail extract, Hedera Helix(Ivy) extract, hawthorn extract, Sambucus migra extract, Achillea millefolium extract, Mentha piperita extract, sage extract, mallow extract, Cnidium officinale Root extract, Japanese green gen tian extract, Soybean extract, jujube extract, thyme extract, tea extract, clove extract, Gramineae imperata cyrillo extract, citrus unshiu peel extract, Japanese angelica root extract, calendula extract, peach kernel extract, bitter orange peel extract, Houttuyna cordata extract, tomato extract, natto extract, ginseng extract, green tea extract (camelliea sine sis), garlic extract, wild rose extract, hibiscus extract, Ophiopogon tuber extract, Nelumbo nucifera extract, parsley extract, honey, hamamelis extract, parietaria extract, isodonis herba extract, bisabolol extract, Loquat extract, coltsfoot extract, butterbur extract, Poria cocos wolf extract, extract of butcher's broom, grape extract, propolis extract, lufa extract, safflower extract, peppermint extract, linden tree extract, Paeonia extract, hop extract, pine tree extract, horse chestnut extract, Mizu-bashou Lysichiton camtschatcese extract, Mukurossi peel extract, Melissa extract, peach extract, corn flower extract, eucalyptus extract, saxifrage extract, citron extract, coix extract, mugwort extract, lavender extract, apple extract, lettuce extract, lemon extract, Chinese milk vetch extract, rose extract, rosemary extract, Roman Chamomile extract, and royal jelly extract.

The amount of component (E) present in the polyurethane gel composition may vary, but typically range as follows: 0.05 to 50 wt %, alternatively 1 to 25 wt %, or alternatively 1 to 10 wt %, based on the amount by weight of polyurethane elastomer gel present in the composition, that is total weight of components (A), (B), (C) and (D) in the gel composition.

Component (E) may be added to the polyurethane gel composition either during the making of the polyurethane elastomer (pre-load method), or added after the formation of the polyurethane elastomer gel (post load method).

The pre-load method comprises: reacting: (A) polyisocyanate; (B) polyol; and (C) an optional polyurethane reaction catalyst, optionally in (D) a carrier fluid; and admixing (E) a personal care or healthcare active with the polyurethane elastomer gel to form the polyurethane elastomer gel containing active.

The post-load method comprises: (I) reacting: (A) polyisocyanate; (B) polyol; (C) an optional polyurethane reaction catalyst, optionally in (D) a carrier fluid to form a polyurethane elastomer gel; (II) shearing the polyurethane elastomer gel into a smooth paste; and (III) admixing (E) a personal care or healthcare active ingredient with the polyurethane elastomer gel to form the polyurethane elastomer gel containing active. The personal care active may also be admixed as a component of another mixture with one or more excipients.

Polyurethane Elastomer

The polyurethane elastomers of the present invention are obtainable as polyurethane reaction products of components (A) polyisocyanate, (B) polyol, and (C) an optional polyurethane reaction catalyst, optionally in (D) a carrier fluid. The term "polyurethane reaction" means the addition of a compound containing a hydroxyl group (such as component (A)) to a compound containing an isocyanate group (such as component (B)), in the presence of a catalyst (such as component (C)), wherein the molar ratio of hydroxyl groups to isocyanate groups is 1:1. Alternatively, this ratio can range from 8:1 to 0.9:1. The polyurethane reaction is conducted in the presence of a solvent, where the solvent is the same as the carrier fluid described as component (D) and used without further purification.

In a specific embodiment, the invention provides a crosslinked polyurethane elastomer network according to the following general structure and prepared by the following general scheme (the depicted structure is based on the principle triglyceride component of castor oil, ricinolein), formed from the reaction of castor oil with isophorone diisocyanate:

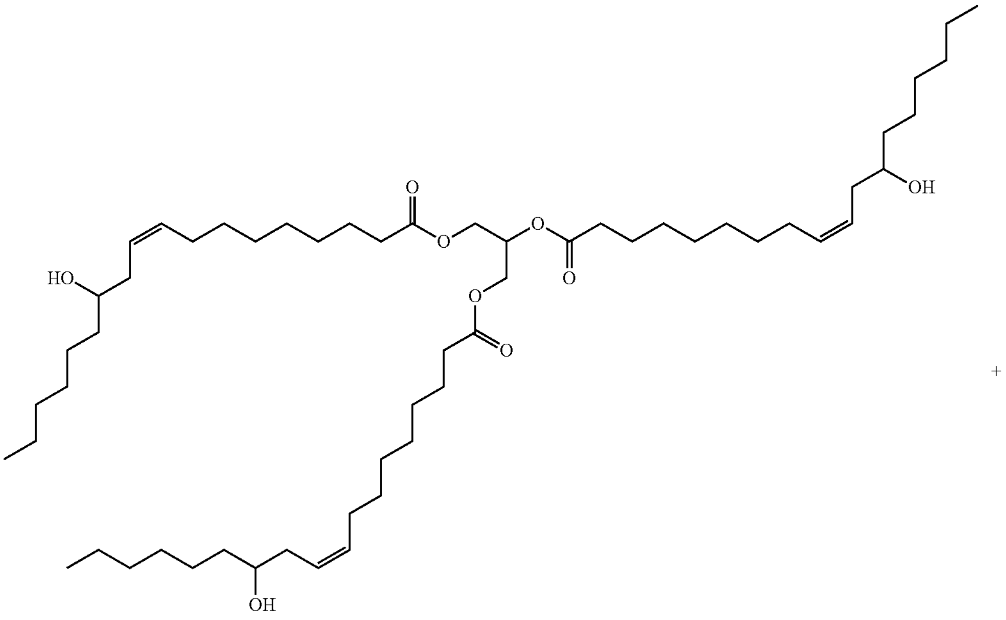

Castor Oil

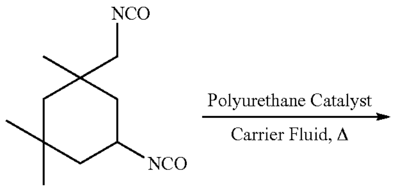

Isophorone Diisocyanate

-continued

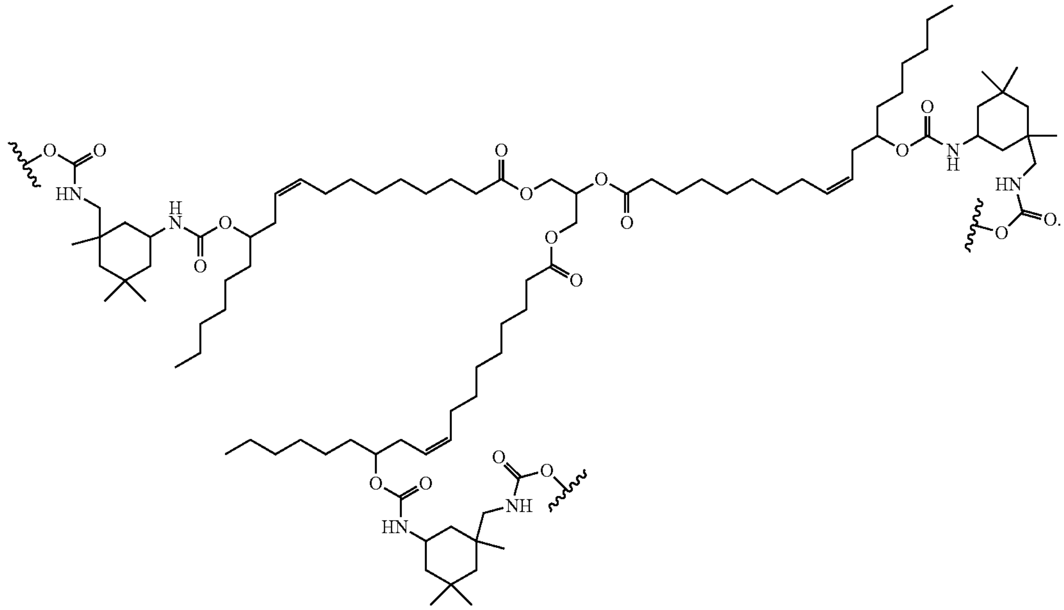

Castor Oil/Isophorone Diisocyanate Polyurethane Elastomer

In a further embodiment, the structure of the polyurethane elastomer is a cross-linked polymer network of the repeat units dilinoleic acid/propane diol copolymer, alkyl carbamate, and triazine trione. A typical chemical structure for the polyurethane polymer network is represented below and formed according to the following reaction scheme:

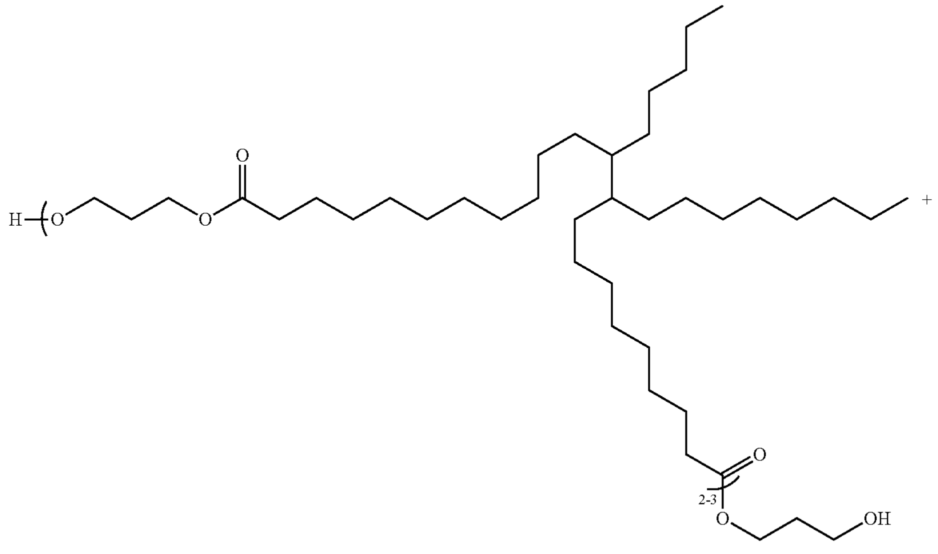

-continued

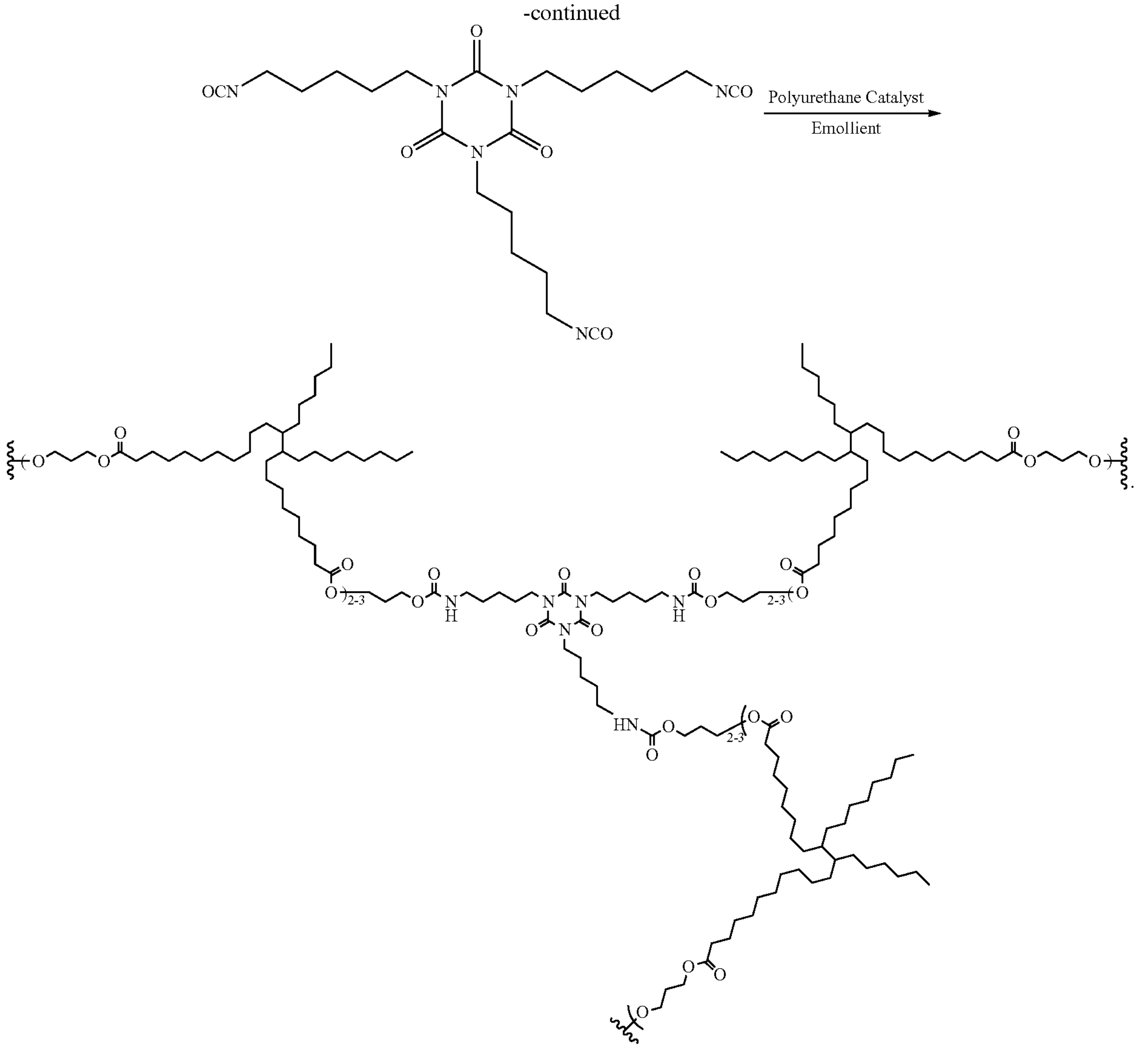

In certain embodiments, the polyurethane elastomer gel described above is prepared in a three-step process. First, dilinoleic acid/propane diol copolymer is reacted with 1,5-pentamethylene diisocyanate trimer in the presence of bismuth neodecanoate in a reaction medium of triheptanoin and coco-caprylate/caprate at elevated temperature with mixing. The molecular weight range of the dilinoleic acid/propane diol copolymer is about 1000-3000. The molar ratios of NCO of the polyisocyanate to OH of the copolymer can be between 2:1 to 1:2. The amount of bismuth neodecanoate in the reaction mixture can approximately be between 0.05-2.25% by weight. The reaction occurs between the hydroxyl groups of the copolymer and the isocyanate groups of the polyisocyanate in the presence of a catalyst to create a urethane linkage —RNHCOOR'—. The product is a cross-linked polyurethane elastomer rubber with the topically acceptable carrier fluids triheptanoin and coco-caprylate/caprate entrapped in the elastomeric matrix. The resulting off-white rubber is soft, not brittle, and slightly sticky to the touch. In the second step, the rubber is diluted with a carrier fluid such as triheptanoin and milled into a gel using a high sheer mixture, a disperser, or a homogenizer. The resulting gel concentrate is thick and smooth, and with no granule particles. When applied to skin the gel is easily absorbed and spreads evenly with no pilling. In the third step, a carrier fluid such as undecane and/or tridecane or coconut alkanes may be added to the gel concentrate with high sheer mixer until the desired viscosity achieved.

The hardness of the polyurethane elastomer rubber is an important factor that determines if it can be readily processed into a gel. If the polyurethane elastomer rubber is too hard, the rubber granules will not swell properly or grind into a smooth gel upon processing. If the polyurethane elastomer rubber is too soft, it will not easily process into a gel due to stickiness and lack of swellable particles. Five factors mainly determine the hardness of the polyurethane elastomer rubber.

First, the solid content as determined by weight percent of reactants in the synthesis of the polyurethane elastomer rubber is a critical factor that determines the polyurethane elastomer rubbers hardness and gelation capacity. If the solid content is to high the rubber will be hard and brittle. If the solid content is too low the rubber will be sticky and soft. In practice, the total weight percent of reactants in the rubber formation can be between 70-95%.

Second, the identity of the topically acceptable carrier fluid(s) affects polyurethane hardness and processing. If coco-caprylate/caprate is used as the only carrier fluid, the polyurethane elastomer rubber may be too hard and brittle and therefore will not process into a smooth gel. Using triheptanoin or a mixture of triheptanoin and coco-caprylate/caprate in ratios of 4:1 to 1:1 can produce a polyurethane elastomer rubber with appropriate hardness. Preferably a ratio of 3:1 is used.

Third, the ratios of polyol to polyisocyanate based polyisocyanate affects the polyurethane elastomer rubber hardness. If the molar ratios of hydroxyl groups to isocyanates is too large or small, sufficient cross-linking will not occur and a soft and sticky product will be formed, which cannot be processed into a gel. The molar ratios of NCO of said isocyanate to OH of said polyol can be between 2:1 to 1:2.

Fourth, the amount of bismuth catalyst used in the synthesis of the polyurethane elastomer rubber is another factor that determines its ability to be processed into a gel. If too much catalyst is used the rubber will over-cure while heating and will be too hard to be processed into a gel. If too little catalyst is used the rubber will not form. In practice, the amount of bismuth catalyst can be about 0.05-2.25% by weight.

Fifth, the reaction temperature should not exceed 80° C. or the elastomer rubber may over cure, resulting in a rubber that is too hard. In addition, weeping of the solvent may occur at temperatures above 80° C. The reaction temperature for rubber formation should be about 40-80° C.

Methods for Measuring Viscosity of Polyurethane Elastomer Gel Paste

The Brookfield HELIPATH™ Stand, when used with a suitable Brookfield Viscometer fitted with a special T-bar type spindle, will permit viscosity/consistency measurements in centipoise values for materials having characteristics similar to paste, putty, cream, gelatin, or wax. The viscosity of polyurethane elastomer blends was determined using a Brookfield Model DV-II+Pro Viscometer with HELIPATH™ stand (Brookfield Model D) and T-Bar spindles (Brookfield HELIPATH™ Spindle Set). All were purchased from Brookfield Engineering Laboratories, Inc. (11 Commerce Boulevard Middleboro, Mass., USA). A sample size of 50 g in a 4-ounce round jar was required. The following preparation procedure was used before measurement: air bubbles were removed from samples first via centrifuge and then under vacuum for two hours. After de-airing, the sample was conditioned for a minimum of 4 hours at 25° C. The measurement was taken according to the typical procedure for a HELIPATH™ spindle. In general, spindle 93 (T-bar spindle E) is used and the standard setting for rpm was 6.5. The spindle speed is maintained at constant 6.5 rpm.

Topical Formulations

Topical formulations comprising the gel compositions or gel pastes are also provided herein. In such formulations, the gel compositions or gel pastes are suitably used as thickeners or stabilizers for the topical formulations. Other components of the topical formulations are known in the art, and can include for example, various components such as emulsion stabilizers, emulsifiers skin conditioners, suspending agents etc. The amounts of these additional components can be on the order of about 0.01% to about 50% by weight.

As used herein, an "emulsion stabilizer" refers to a composition that aids in keeping an emulsion from separating into its oil and aqueous components. In embodiments, the emulsion stabilizer utilized in the formulations described herein is a naturally derived gum or a modified gum or natural mineral. Exemplary emulsion stabilizers include, but are not limited to, acacia, cellulose, crystalline cellulose, gellan, guar, locust (carob) bean, xanthan, magnesium aluminum silicate, bentonite or hectorite clays and the like, including combinations thereof.

As used herein, a "skin conditioner" refers to a composition that acts as a lubricant on the surface of the skin or a composition that increases the water content of the surface of the skin. Exemplary skin conditioners for use in the formulations include, but are not limited to, adipate esters, alkyl benzoates, fatty acid esters of C8 or greater, esterified erucates, laurates, neopentanoates, salicylates, stearates, triglycerides, carbonates, glycols, glycerin, mineral oils and the like, including combinations thereof.

As used herein, an "emulsifier" refers to a composition that aids in the formation of an oil in water, or a water in oil, emulsion. Exemplary emulsifiers for use in the formulations include, but are not limited to, polysorbates, ethoxylated fatty acids, fatty acids neutralized with sodium hydroxide, potassium hydroxide or amines, substituted glucosides, sodium lauryl and lauryl ether sulfates, ethoxylated esters, lecithin and lecithin derivatives and the like, including combinations thereof.

As used herein, a "suspending agent" refers to a composition that modifies the interface between solid particles and a liquid medium to improve the particles' resistance to coming together and falling out of solution. Exemplary suspending agents for use in the formulations include, but are not limited to, hydroxy stearic acid, polyhydroxystearic acid, sodium polyacrylate polymers, methyl methacrylate crosspolymers and the like, including combinations thereof.

In additional embodiments, the polyurethane elastomers can be utilized in solid-based formats, including for example, as a foot conforming shoe insert or shoe sole.

EXEMPLARY EMBODIMENTS

Embodiment 1: A gel composition comprising a polyurethane elastomer gel prepared from the reaction of:
- (A) a polyisocyanate or a mixture of polyisocyanates comprising two or more isocyanate functional groups;
- (B) a polyol or mixture of polyols comprising two or more hydroxyl, amine, thiol, or carboxylic acid functional groups;
- (C) an optional polyurethane reaction catalyst; and
- (D) an optional topically acceptable carrier fluid.

Embodiment 2: The gel composition of embodiment 1, wherein the topically acceptable carrier fluid is selected from the group consisting of esters, triglycerides, hydrocarbons, silicone fluids, oils, and combinations thereof.

Embodiment 3: The gel composition of embodiment 1, wherein the topically acceptable carrier fluid is selected from the group consisting of diisooctyl succinate, heptyl undecylenate, neopentyl glycol diheptanoate, coco-caprylate/caprate, triheptanoin, caprylic/capric triglyceride, dodecane, tridecane, C13-15 alkane, squalene, squalene, isoamyl laurate, isopentyl laurate, caprylic/capric/myristic/stearic triglyceride, caprylic/capric/succinic triglyceride, isopropyl myristate, jojoba esters, tricaprylin, and palm oil.

Embodiment 4: The gel composition of embodiment 1, further comprising a pharmaceutically active ingredient dissolved in the topically acceptable carrier fluid.

Embodiment 5: The gel composition of embodiment 1 wherein the polyisocyanate or mixture of polyisocyanates is a low molecular weight polyisocyanate or mixture of polyisocyanates and wherein the polyol or mixture of polyols contains two or more hydroxyl, amine, thiol, or carboxylic acid groups.

Embodiment 6: A gel composition comprising a polyurethane elastomer from the reaction of:
(A) castor oil;
(B) isophorone diisocyanate, wherein the molar ratio of isocyanate groups to hydroxyl groups is between 1:1 and 1:2;
(C) an optional polyurethane reaction catalyst; and
(D) a topically acceptable carrier fluid at a concentration of 60% (w/w) to 99.9% (w/w) of the gel composition;
wherein a personal care or healthcare active ingredient is optionally incorporated into the polyurethane elastomer gel by dissolving the personal care or healthcare active ingredient in the topically acceptable solvent during the formation of the polyurethane elastomer gel, or by admixing the personal care or healthcare active ingredient with a formed polyurethane elastomer gel.

Embodiment 7: The gel composition of embodiment 6, wherein the topically acceptable carrier fluid is selected from the group consisting of esters, triglycerides, hydrocarbons, silicone fluids, and combinations thereof.

Embodiment 8: The gel composition of embodiment 6, wherein the topically acceptable carrier fluid is selected from the group consisting of diisooctyl succinate, heptyl undecylenate, neopentyl glycol diheptanoate, and coco-caprylate/caprate.

Embodiment 9: The gel composition of embodiment 6, further comprising a pharmaceutically active ingredient dissolved in the topically acceptable carrier fluid.

Embodiment 10: The gel composition of embodiment 1, wherein the polyurethane catalyst is a bismuth group containing catalyst.

Embodiment 11: The gel composition of embodiment 6, wherein the polyurethane catalyst is a bismuth group containing catalyst.

Embodiment 12: The gel composition of embodiment 1, wherein greater than 50% of the carbon content of the topically acceptable solvent is derived from plant sources.

Embodiment 13: The gel composition of embodiment 6, wherein greater than 50% of the carbon content of the topically acceptable solvent is derived from plant sources.

Embodiment 14: A process for preparing the gel composition of embodiment 1, comprising reacting:
(A) a polyol;
(B) isophorone diisocyanate; and
(C) an optional polyurethane reaction catalyst;
optionally in the presence of
(D) a topically acceptable carrier fluid.

Embodiment 15: A process for preparing the gel composition of embodiment 6, comprising reacting:
(A) castor oil;
(B) isophorone diisocyanate; and
(C) an optional polyurethane reaction catalyst;
optionally in the presence of
(D) a topically acceptable carrier fluid.

Embodiment 16: A gel composition prepared according to the process of embodiment 14.

Embodiment 17: A gel composition prepared according to the process of embodiment 15.

Embodiment 18: A process for preparing a gel paste composition, comprising:
(I) shearing the gel composition of embodiment 1, and
(II) combining the sheared polyurethane elastomer gel with an additional quantity of the carrier fluid to form a gel paste composition.

Embodiment 19: A process for preparing a gel paste composition comprising:
(I) shearing the gel composition of embodiment 1, and
(II) combining the sheared polyurethane elastomer gel with an active ingredient.

Embodiment 20: A process for preparing a gel paste composition, comprising:
(I) shearing the gel composition of embodiment 6, and
(II) combining the sheared polyurethane elastomer gel with an additional quantity of the carrier fluid to form a gel paste composition.

Embodiment 21: A process for preparing a gel paste composition comprising:
(I) shearing the gel composition of embodiment 6, and
(II) combining the sheared polyurethane elastomer gel with an active ingredient.

Embodiment 22: A method of making a polyurethane elastomer comprising:
I) mixing a polyisocyanate reactant and a polyol reactant, optionally in a topically acceptable carrier fluid to form a reaction mixture with a reactant concentration of about 80% (w/w), wherein the polyciso-cyanate reactant comprises two or more isocyanate functional groups and the polyol reactant comprises two or hydroxyl groups;
II) optionally adding a polyurethane reaction catalyst; and
III) optionally heating the reaction mixture to about 80° C. to form the polyurethane elastomer.

Embodiment 23: The method of embodiment 22, wherein the topically acceptable carrier fluid is selected from the group consisting of esters, triglycerides, hydrocarbons, silicone fluids, and combination thereof.

Embodiment 24: The method of embodiment 22, wherein the topically acceptable carrier fluid is selected from the group consisting of diisooctyl succinate, heptyl undecylenate, neopentyl glycol diheptanoate, coco-caprylate/caprate, and combination thereof.

Embodiment 25: The method of embodiment 22, further comprising dissolving a pharmaceutically active ingredient in the topically acceptable carrier fluid.

Embodiment 26: The method of embodiment 22, wherein the polyisocyanate reactant is derived from the polymerization of another polyisocyanate.

Embodiment 27: The method of embodiment 22, further comprising preparing the polyisocyanate reactant from hexamethylene diisocyanate.

Embodiment 28: The method of embodiment 22, further comprising preparing the polyisocyanate reactant from pentamethylene diisocyanate.

Embodiment 29: A polyurethane elastomer gel paste prepared by the method of embodiment 18.

Embodiment 30: A polyurethane elastomer gel paste prepared by the method of embodiment 19.

Embodiment 31: A polyurethane elastomer gel paste prepared by the method of embodiment 20.

Embodiment 32: A polyurethane elastomer gel paste prepared by the method of embodiment 21.

Embodiment 33: A topical formulation comprising:
the gel composition of embodiment 1 or embodiment 6; and a pharmaceutically active ingredient, wherein the pharmaceutically active ingredient is a personal care active ingredient or a healthcare active ingredient.

Embodiment 34: A topical formulation comprising:

the polyurethane elastomer gel paste of any of embodiments 29 to 32; and a pharmaceutically active ingredient, wherein the pharmaceutically active ingredient is a personal care active ingredient or a healthcare active ingredient.

Embodiment 35: A foot conforming shoe insert or shoe sole comprising the gel composition of embodiment 1 or embodiment 6.

Embodiment 36: A medical medically acceptable gel comprising the gel composition of embodiment 1 or embodiment 6.

Embodiment 37: A topical formulation comprising the gel composition of embodiment 1 or embodiment 6.

The disclosure is further illustrated by the following examples which are provided merely to be exemplary and do not limit the scope of the invention. Certain modifications and equivalents will be apparent to those skilled in the art and are intended to be included within the scope of the disclosure. The present disclosure provides, but is not limited to, the following formulation examples.

Example 1—Preparation of Dilinoleic Acid/Propane Diol Copolymer Based Polyurethane Elastomer Gel with Triheptanoin, Coco-Caprylate/Caprate, and Undecane (and) Tridecane To a reaction kettle was added triheptanoin, coco-caprylate/caprate, dilinoleic acid/propane diol copolymer, and pentamethylene diisocyanate trimer. This mixture was stirred at room temperature until a clear, homogeneous solution was obtained. Bismuth neodecanoate was added with stirring, and the reaction was heated to 60° C. for about 1 hour, at which point an off-white soft rubber is formed. After rubber formation the rubber is allowed to cool to room temperature.

The polyurethane elastomer rubber was then placed in a drum, triheptanoin was added with high sheer mixing. The resulting suspension was then run through a disperser and the resulting gel was allowed to cool to room temperature. Undecane and/or tridecane were then added with mixing until the desired viscosity was achieved.

Example 2—Preparation of Dilinoleic Acid/Propane Diol Copolymer Based Polyurethane Elastomer Gel with Triheptanoin, Coco-Caprylate/Caprate, and Coconut Alkanes Prepare a polyurethane elastomer rubber according to Example 1. The polyurethane elastomer gel is prepared by placing the polyurethane elastomer rubber in a drum, then triheptanoin was added with high sheer mixing. The resulting suspension was then run through a disperser and the resulting gel was allowed to cool to room temperature. Coconut alkanes were then added with mixing until the desired viscosity was achieved.

Example 3—Preparation of Dilinoleic Acid/Propane Diol Copolymer Based Polyurethane Elastomer Gel with Triheptanoin, and Coco-Caprylate/Caprate Prepare a polyurethane elastomer rubber according to Example 1. The polyurethane elastomer gel is prepared by placing the polyurethane elastomer rubber in a drum, then triheptanoin was added with high sheer mixing. The resulting suspension was then run through a disperser and the resulting gel was allowed to cool to room temperature. Coco-caprylate/caprate were then added with mixing until the desired viscosity was achieved.

Example 4—Preparation of Dilinoleic Acid/Propane Diol Copolymer Based Polyurethane Elastomer Gel with Triheptanoin Prepare a polyurethane elastomer rubber according to Example 1. The polyurethane elastomer gel is prepared by placing the polyurethane elastomer rubber in a drum, then triheptanoin was added with high sheer mixing. The resulting suspension was then run through a disperser and the resulting gel was allowed to cool to room temperature. Triheptanoin were then added with mixing until the desired viscosity was achieved.

Example 5—Preparation of Castor Oil Based Pentamethylene Diisocyanate Trimer Polyurethane Elastomer To ajar was added triheptanoin, castor oil, and pentamethylene diisocyanate trimer. This mixture was stirred at room temperature until a clear, homogeneous solution was obtained. Bismuth neodecanoate was added with stirring, and the reaction was heated to 60° C. for about 1 hour, at which point an off-white soft rubber is formed. After rubber formation the rubber was allowed to cool to room temperature.

The polyurethane elastomer rubber was then placed in a steel container and triheptanoin was added with high sheer mixing until the desired viscosity was achieved.

In a certain example, to a stainless steel reaction vessel was added triheptanoin (202.0 grams), castor oil (32.0 grams), pentamethylene diisocyanate trimer (15.9 grams), and bismuth neodecanoate (2.5 grams). This mixture was vigorously stirred at room temperature for about 20 minutes until a clear, homogeneous mixture was obtained. The reaction mixture was placed in an aluminum container and heated to 80° C. for 1 hour, at which point a translucent rubber was formed.

The polyurethane elastomer rubber was then broken into smaller pieces, placed in a metal container, and triheptanoin added before homogenization into a smooth gel paste with a desired viscosity using a Silverson L5M-A homogenizer with a 30 mm diameter rotor, Square Hole High Shear Screen, and operating at 4500 to 8000 revolutions per minute.

In another example, to a 4 ounce glass jar was added triheptanoin (41.1 grams), castor oil (6.7 grams), pentamethylene diisocyanate trimer (3.31 grams), and bismuth neodecanoate (0.5 grams). This mixture was vigorously stirred at room temperature for about 10 minutes until a clear, homogeneous mixture was obtained. The reaction mixture was covered and heated to 80° C. for 19.5 hours, at which point a translucent rubber was formed. The hardness of the 50 gram sample of gel was 1.72 N, as determined using a Stable Micro Systems Texture Analyzer with a 5 kilogram load cell, fitted with a TA-18B Stable Micro Systems probe, and inserted 5 mm into the gel surface.

Example 6—Preparation of Castor Oil/Isophorone Diisocyanate Polyurethane Elastomer To a stainless steel reaction vessel was added diisooctyl succinate (440 grams), castor oil (71.1 grams) with hydroxyl value of 166.87 mg/g, isophorone diisocyanate (23.5 grams) with 37.80% isocyanate content, and bismuth neodecanoate (5.33 grams). This mixture was vigorously stirred at room temperature for about 20 minutes until a clear, homogeneous mixture was obtained and 50 grams of the mixture poured into a 4 ounce glass jar. The remainder of the reaction mixture and the 50 gram sample were heated to 75° C. for 18 hours, at which point a translucent gel formed. The hardness of the 50 gram sample of gel was 2.85 N, as determined using a Stable Micro Systems Texture Analyzer with a 5 kilogram load cell, fitted with a TA-18B Stable Micro Systems probe, and inserted 5 mm into the gel surface.

The polyurethane elastomer gel was then broken into smaller pieces, placed in a metal container, and heptyl undecylenate added before homogenization into a smooth gel paste with a desired viscosity using a Silverson L5M-A homogenizer with a 30 mm diameter rotor, Square Hole High Shear Screen, and operating at 4500 to 8000 revolutions per minute.

In a certain example, to a glass reaction vessel was added triheptanoin (293.5 grams), castor oil (87.9 grams) with hydroxyl value of 166.87 mg/g, isophorone diisocyanate (29.0 grams) with 37.80% isocyanate content, and bismuth neodecanoate (8.9 grams). This mixture was vigorously stirred at room temperature for about 20 minutes until a clear, homogeneous mixture was obtained and 50 grams of the mixture poured into a 4 ounce glass jar. The remainder of the reaction mixture and the 50 gram sample were covered and heated to 75° C. for 19.5 hours, at which point a translucent rubber was formed. The hardness of the 50 gram sample of gel was 3.69 N, as determined using a Stable Micro Systems Texture Analyzer with a 5 kilogram load cell, fitted with a TA-18B Stable Micro Systems probe, and inserted 5 mm into the gel surface.

The polyurethane elastomer rubber was then broken into smaller pieces, placed in a metal container, and triheptanoin added before homogenization into a smooth gel paste with a desired viscosity using a Silverson L5M-A homogenizer with a 30 mm diameter rotor, Square Hole High Shear Screen, and operating at 4500 to 8000 revolutions per minute.

Example 7—Preparation of Dilinoleic Acid/Propane Diol Copolymer Based Hexamethylene Diisocyanate Trimer Elastomer To a plastic reaction vessel was added heptyl undecylenate (1959.2 g grams), dilinoleic acid/propane diol copolymer (410.0 grams) with hydroxyl value of 56 mg/g, hexamethylene diisocyanate trimer (70.0 grams) with 22.77% isocyanate content, and bismuth neodecanoate (10.0 grams). This mixture was vigorously stirred at room temperature for about 20 minutes until a clear, homogeneous mixture was obtained and 50 grams of the mixture poured into a 4 ounce glass jar. The remainder of the reaction mixture and the 50 gram sample were covered and left at 25° C. for 25 hours, at which point a translucent rubber was formed. The hardness of the 50 gram sample of gel was 3.14 N, as determined using a Stable Micro Systems Texture Analyzer with a 5 kilogram load cell, fitted with a TA-18B Stable Micro Systems probe, and inserted 5 mm into the gel surface.

The polyurethane elastomer rubber was then broken into smaller pieces, placed in a metal container, and heptyl undecylenate added before homogenization into a smooth gel paste with a desired viscosity using a Silverson L5M-A homogenizer with a 30 mm diameter rotor, Square Hole High Shear Screen, and operating at 4500 to 8000 revolutions per minute.

Example 8—Preparation of Dilinoleic Acid/Propane Diol Copolymer Based Pentamethylene Diisocyanate Trimer Elastomer To a stainless steel reaction vessel was added coco-caprylate/caprate (445.0 grams), dilinoleic acid/propane diol copolymer (87.5 grams), pentamethylene diisocyanate trimer (20.6 grams), and bismuth neodecanoate (3.2 grams). This mixture was vigorously stirred at room temperature for about 10 minutes until a clear, homogeneous mixture was obtained. The reaction mixture heated to 80° C. for 1 hour, at which point a translucent rubber was formed.

The polyurethane elastomer rubber was then broken into smaller pieces, placed in a metal container, and coco-caprylate/caprate added before homogenization into a smooth gel paste with a desired viscosity using a Silverson L5M-A homogenizer with a 30 mm diameter rotor, Square Hole High Shear Screen, and operating at 4500 to 8000 revolutions per minute.

In a certain example, to a 4 ounce glass jar was added coco-caprylate/caprate (39.5 grams), dilinoleic acid/propane diol copolymer (7.8 grams) with hydroxyl value of 56 mg/g, pentamethylene diisocyanate trimer (1.8 grams) with 23.5% isocyanate content, and bismuth neodecanoate (0.3 grams). This mixture was vigorously stirred at room temperature for about 10 minutes until a clear, homogeneous mixture was obtained. The reaction mixture was covered and the heated to 80° C. for 19.5 hours, at which point a translucent rubber was formed. The hardness of the 50 gram sample of gel was 7.12 N, as determined using a Stable Micro Systems Texture Analyzer with a 5 kilogram load cell, fitted with a TA-18B Stable Micro Systems probe, and inserted 5 mm into the gel surface.

Example 9—Preparation of a Castor Oil Based Hexamethylene Diisocyanate Trimer Elastomer To a plastic reaction vessel was added triheptanoin (2354.7 grams), castor oil (373.0 grams), hexamethylene diisocyanate trimer (188.6 grams) with 22.77% isocyanate content, and bismuth neodecanoate (27.0 grams). This mixture was vigorously stirred at room temperature for about 20 minutes until a clear, homogeneous mixture was obtained and 50 grams of the mixture poured into a 4 ounce glass jar. The remainder of the reaction mixture and the 50 gram sample were covered and left at room temperature for 20 hours, at which point a translucent rubber was formed. The hardness of the 50 gram sample of gel was 2.72 N, as determined using a Stable Micro Systems Texture Analyzer with a 5 kilogram load cell, fitted with a TA-18B Stable Micro Systems probe, and inserted 5 mm into the gel surface.

The polyurethane elastomer rubber was then broken into smaller pieces, placed in a metal container, and triheptanoin added before homogenization into a smooth gel paste with a desired viscosity using a Silverson L5M-A homogenizer with a 30 mm diameter rotor, Square Hole High Shear Screen, and operating at 4500 to 8000 revolutions per minute.

Example 10—Preparation of Dilinoleic Acid/Dilinoleic Diol Copolymer Based Hexamethylene Diisocyanate Trimer Elastomer To a glass reaction vessel was added coco-caprylate/caprate (826.3 g grams), dilinoleic acid/dilinoleic diol copolymer (172.8 grams) with hydroxyl value of 56 mg/g, hexamethylene diisocyanate trimer (29.5 grams) with 22.77% isocyanate content, and bismuth neodecanoate (4.23 grams). This mixture was vigorously stirred at room temperature for about 20 minutes until a clear, homogeneous mixture was obtained and 50 grams of the mixture poured into a 4 ounce glass jar. The remainder of the reaction mixture and the 50 gram sample were covered and heated to 75° C. for 17 hours, at which point a translucent rubber was formed. The hardness of the 50 gram sample of gel was 4.51 N, as determined using a Stable Micro Systems Texture Analyzer with a 5 kilogram load cell, fitted with a TA-18B Stable Micro Systems probe, and inserted 5 mm into the gel surface.

The polyurethane elastomer rubber was then broken into smaller pieces, placed in a metal container, and coco-caprylate/caprate added before homogenization into a smooth gel paste with a desired viscosity using a Silverson L5M-A homogenizer with a 30 mm diameter rotor, Square Hole High Shear Screen, and operating at 4500 to 8000 revolutions per minute.

Example 11—Preparation of Dilinoleic Acid/Dilinoleic Diol Copolymer Based Pentamethylene Diisocyanate Trimer Elastomer To a glass reaction vessel was added coco-caprylate/caprate (231.6 g grams), dilinoleic acid/dilinoleic diol copolymer (49.0 grams) with hydroxyl value of 56 mg/g, pentamethylene diisocyanate trimer (7.7 grams) with 23.5% isocyanate content, and bismuth neodecanoate (1.2 grams). This mixture was vigorously stirred at room temperature for about 20 minutes until a clear, homogeneous mixture was obtained and 50 grams of the mixture poured into a 4 ounce glass jar. The remainder of the reaction mixture and the 50 gram sample were covered and heated to 80° C. for 19.5 hours, at which point a translucent rubber was formed. The hardness of the 50 gram sample of gel was 0.49 N, as determined using a Stable Micro Systems Texture Analyzer with a 5 kilogram load cell, fitted with a TA-18B Stable Micro Systems probe, and inserted 5 mm into the gel surface.

The polyurethane elastomer rubber was then broken into smaller pieces, placed in a metal container, and coco-caprylate/caprate added before homogenization into a smooth gel paste with a desired viscosity using a Silverson L5M-A homogenizer with a 30 mm diameter rotor, Square Hole High Shear Screen, and operating at 4500 to 8000 revolutions per minute.

Example 12—Formulation of Polyurethane Elastomers

To explore the ability to formulate the polyurethane elastomers described herein as topical formulations, the following experiments were performed.

Table 1 below provides exemplary polyurethane elastomers of the present specification ("biolastomers"), along with comparison elastomers. The compositions in Table 1 omit the isocyanate cross-linking agent for Biolastomers A and C, which is hexamethylene diisocyanate trimer. For Biolastomers D, IPDI is isophorone diisocyanate.

TABLE 1

Elastomers Examined

| | Name | Composition |
|---|---|---|
| Disclosed Herein | Biolastomer A | Dilinoleic Acid/Propane Diol Copolymer Crosspolymer (and) Heptyl Undecylenate (and) C13-15 Alkane |
| | Biolastomer C | Dilinoleic Acid/Dilionoleic Diol Copolymer Crosspolymer (and) Coco-caprylate/Caprate |
| | Biolastomer D | Castor Oil/IPDI Copolymer (and) Diisooctyl Succinate (and) Heptyl Undecylenate |
| Comparison | Velvesil* DM | Dimethicone (and) Cetearyl Dimethicone Crosspolymer |
| | Dowsil 9040 | Cyclopentasiloxane (and) Dimethicone Crosspolymer |

The biolastomers described above were added to the following common topical carriers to determine their ability to be formulated as a topical formulation.

In FIG. 1, a scoring system of 5 to 1 was utilized, with a score of "5" indicating a hard gel, a score of "1" indicating a flowable gel. At the amounts studied, the Biolastomers described herein showed good compatibility with: Fatty alcohol>Triglyceride>Ester; Less compatibility with hydrocarbon; and NO compatibility with silicone.

The three Biolastomers were then combined with different sunscreen agents to examine their compatibility with an active agent, and their ability for use as a formulation agent. Tables 2-4 describe the results for the three Biolastomers as noted.

TABLE 2

Biolastomer A at 10% Solids

| | UVA Sunscreen | UVB Sunscreen | | Physical Sunscreens | |
|---|---|---|---|---|---|
| Ingredients | Avobenzone | Octocrylene | Homosalate | ZnO | TiO2 |
| Sunscreen % | 5 | 10 | 10 | 10 | 10 |
| C12-15 alkyl benzoate % | 15 | 10 | 10 | 10 | 10 |
| Biolastomer A % | 80 | 80 | 80 | 80 | 80 |
| Observation | Light yellow Clear gel | Clear gel | Clear gel | Opaque gel | Opaque gel |

TABLE 3

| Biolastomer C at 9% Solids | | | | | |
|---|---|---|---|---|---|
| | UVA Sunscreen | UVB Sunscreen | | Physical Sunscreens | |
| Ingredients | Avobenzone | Octocrylene | Homosalate | ZnO | TiO2 |
| Sunscreen % | 5 | 10 | 10 | 10 | 10 |
| C12-15 alkyl benzoate % | 10 | 5 | 5 | 5 | 5 |
| Biolastomer C % | 85 | 85 | 85 | 85 | 85 |
| Observation | Light yellow translucent gel | Translucent gel | Translucent gel | Opaque gel | Opaque spongy gel |

TABLE 4

| Biolastomer D at 10% Solids | | | | | |
|---|---|---|---|---|---|
| | UVA Sunscreen | UVB Sunscreen | | Physical Sunscreens | |
| Ingredients | Avobenzone | Octocrylene | Homosalate | ZnO | TiO2 |
| Sunscreen % | 5 | 10 | 10 | 10 | 10 |
| C12-15 alkyl benzoate % | 25 | 20 | 20 | 20 | 20 |
| Biolastomer D % | 70 | 70 | 70 | 70 | 70 |
| Observation | Light yellow Clear gel | Clear gel | Clear gel | Opaque gel | Opaque gel |

The results of these experiments indicate that the Biolastomers described herein are highly compatible with organic and physical sunscreens and do not negatively impact the clarity of final formulations.

The processability of the Biolastomers was then evaluated as follows in both oil-in-water emulsions, and water-in-oil emulsions.

TABLE 5

| Processability of 5% Elastomer Gels in Water-in-Oil (W/O) Emulsions | | | |
|---|---|---|---|
| Phase | Ingredients | INCI Name | WT (%) |
| A | Water | Aqua | Up to 100.0 |
| | Glycerin | Glycerin | 3.0 |
| | Sodium Chloride | Sodium Chloride | 1.0 |
| | Y-20537 | Caprylic/Capric Triglycerides (and) PEG/PPG-20/15 Dimethicone | 4.0 |
| B | Neossance Hemisqualane | C13-15 Alkane (emollient) | 5.0 |
| | Blooming Feel In2 | Isononyl Isononanoate (emollient) | 3.0 |
| | Cetiol E | PPG-15 Stearyl Ether (emollient) | 2.0 |
| | Elastomer gel * | | 5.0 |
| | Silsoff 034 fluid | Caprylyl Methicone (emollient) | 2.0 |
| C | Preservative | Preservative | q.s. |

Each of the following elastomer gels* were investigated: Biolastomer A; Biolastomer C; Biolastomer D; Velvesil DM gel; and Dowsil 9040. All the elastomer gels were added into the formulations as premixes with Caprylyl Methicone to the oil phase (B). Premixes were homogenized before addition. Small particles of the elastomer were visible in the premixes, but were not in the products. Phase A was added very slowly to the phase B at high mixing (cold process, standard w/Si emulsion preparation). No major differences were observed during processability of any of elastomer gels in w/o emulsion, confirming that the biolastomers described herein can be readily processed in water-in-oil emulsions.

The processability of the elastomer gels in oil-in-water emulsions was investigated as follows:

TABLE 6

| Processability of 2.5% Elastomer Gels in Oil-in-Water (O/W) Emulsions | | | |
|---|---|---|---|
| Phase | Ingredients | INCI Name | WT (%) |
| A | Water | Aqua | Up to 100.0 |
| | Glycerin | Glycerin | 3.0 |
| | Disodium EDTA | Disodium EDTA | 0.05 |
| B | Arlacel 165 | Glyceryl Staerate/PED-100 Stearate | 3.0 |
| | Cutina GMS | Glyceryl Stearate | 1.5 |
| | Lanette O | Cetearyl Alcohol | 1.5 |
| | *Elastomer gel | | 2.5 |
| | Cetiol E | PPG-15 Staeryl Ether | 4.0 |
| | Blooming Feel In2 | Isononyl Isononanoate | 4.0 |
| | Neossance Hemisqualane | C13-15 Alkane | 4.0 |
| C | Carbopol Ultrez 10 | Carbomer | 0.2 |
| | Water | Aqua | 10.0 |
| | TEA | TEA | 0.2 |
| D | Preservative | | q.s. |

Each of the following elastomer gels* were investigated: Control—No elastomer; Biolastomer C; Biolastomer D; Biolastomer A; Velvesil DM 6; and DM 9040. Water (A) and oil (B) phases were heated separately up to 70° C., then mixed and homogenized. At 50° C. the premix of Carbomer was added, mixed and neutralized. Premixing was required for biolastomers C and D, but no premix was required for Biolastomer, Velvesil DM 6, and DM 9040. Results of the experiments indicated that the ease of processability was, from greatest to least, Velvesil DM>DC 9040>Biolastomer A>Biolastomer C~Biolastomer D.

The sensory (skin feel) characteristics of the elastomers were also evaluated. The results indicated the following: Control—"flat" sensory, no cushioning; Biolastomer C—provides smooth cushioning sensory, moisturized, and not dry. The skin is soft; Biolastomer D—a bit shiny and lubricious, after feel is smooth, elastic and cushioning; Biolastomer A—in between C and D; Velvesil DM—powdery and dry cushioning sensory, matting benefits; Dowsil 9040—powdery but elastic cushioning, less dry than Velvesil DM, provides matting benefits.

The following are also evaluated for the elastomer formulations: Rheology: shear-thinning behavior of Biolastomers; Ease of production: Prepare a kilogram of Biolastomer in an emollient using Ross Mixer and in-line homogenizer and Evaluate shear sensitivity.

Example 13—Fourier-Transform Infrared Spectroscopy of Polyurethane Elastomers Fourier-Transform Infrared Spectroscopy (FTIR) was performed to analyze the molecular structures of the polyurethane elastomers.

The FTIR spectrograph of dilinoleic acid/propane diol copolymer based pentamethylene diisocyanate trimer elastomer is shown in FIG. 1.

The FTIR spectrograph of dilinoleic acid/propane diol copolymer based hexamethylene diisocyanate trimer elastomer is shown in FIG. 2.

Figure 3:
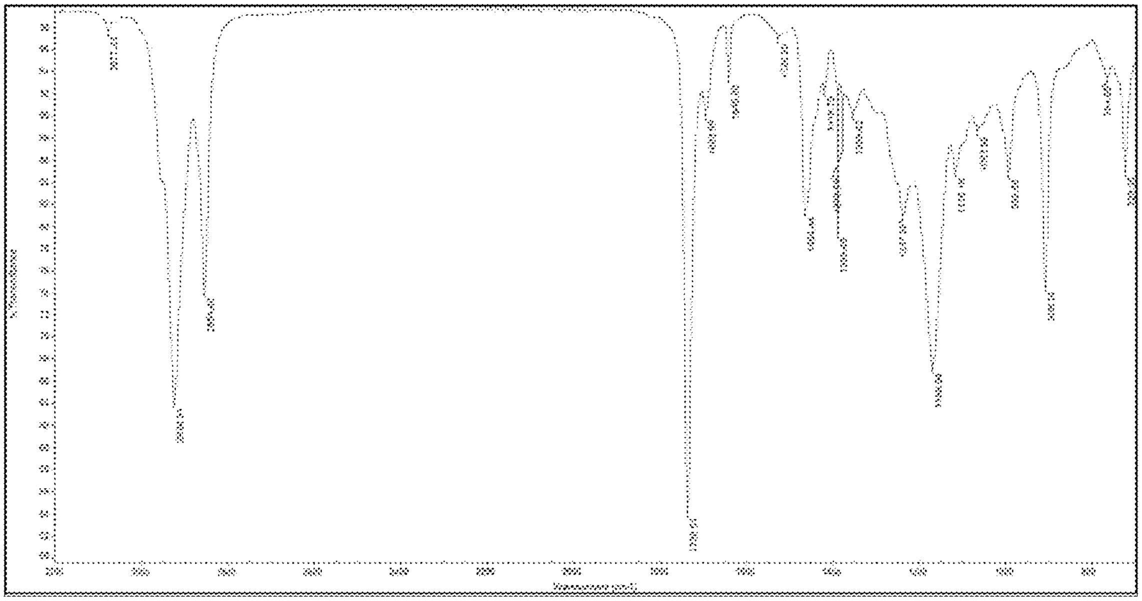
FIG. 3 shows a FTIR spectrograph of dilinoleic acid/propane diol copolymer based hexamethylene diisocyanate trimer elastomer, as described in embodiments herein.

The FTIR spectrograph of castor oil based pentamethylene diisocyanate trimer elastomer is shown in FIG. 3.

Figure 4:
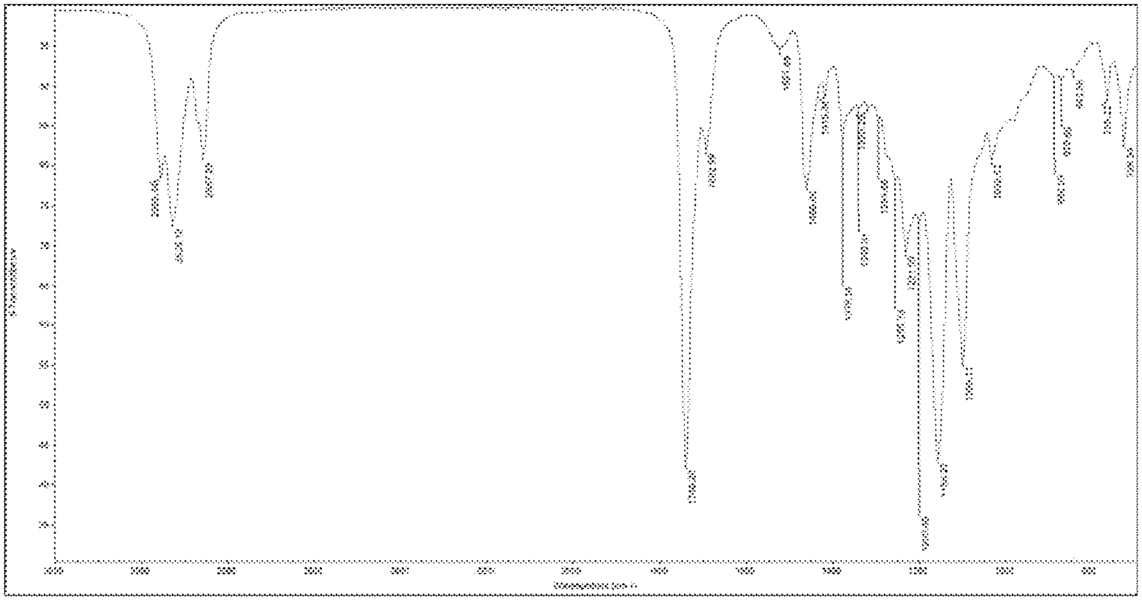
FIG. 4 shows a FTIR spectrograph of castor oil based pentamethylene diisocyanate trimer elastomer, as described in embodiments herein.

The FTIR spectrograph of castor oil based hexamethylene diisocyanate trimer elastomer is shown in FIG. 4.

Figure 5:
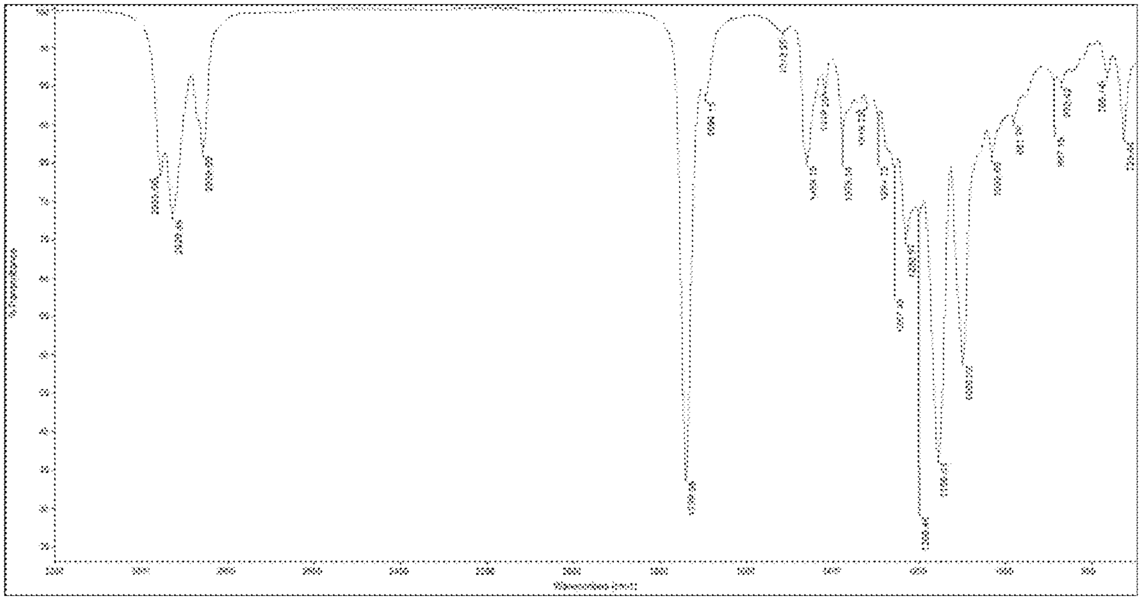
FIG. 5 shows a FTIR spectrograph of castor oil based hexamethylene diisocyanate trimer elastomer, as described in embodiments herein.

The FTIR spectrograph of dilinoleic acid/dilinoleic diol copolymer based pentamethylene diisocyanate trimer elastomer is shown in FIG. 5.

Figure 6:
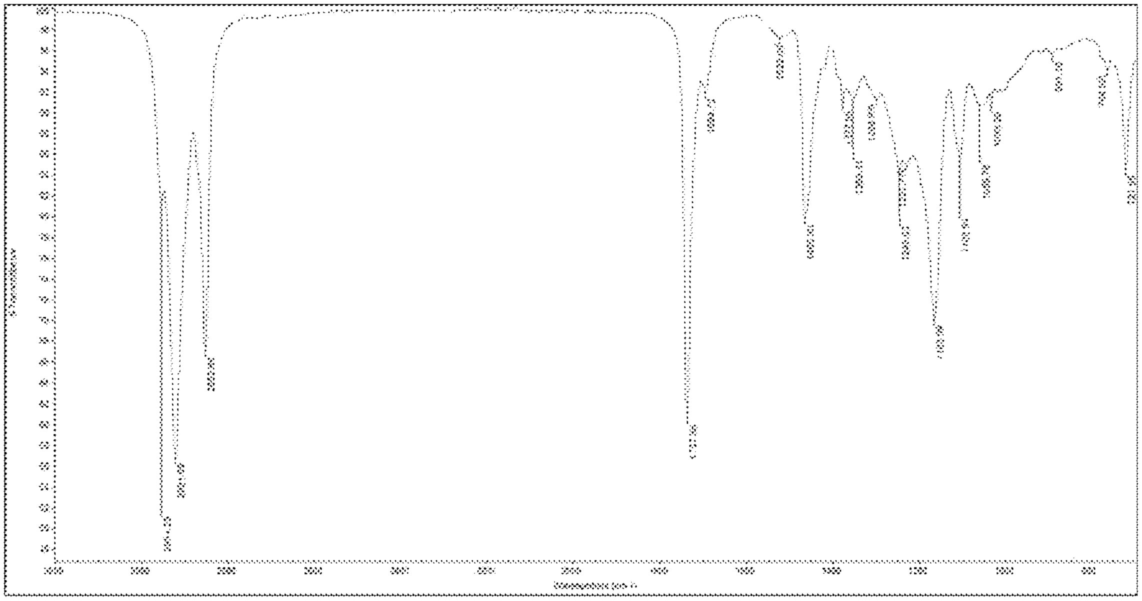
FIG. 6 shows a FTIR spectrograph of dilinoleic acid/dilinoleic diol copolymer based pentamethylene diisocyanate trimer elastomer, as described in embodiments herein.

The FTIR spectrograph of dilinoleic acid/dilinoleic diol copolymer based hexamethylene diisocyanate trimer elastomer is shown in FIG. 6.

Figure 7:
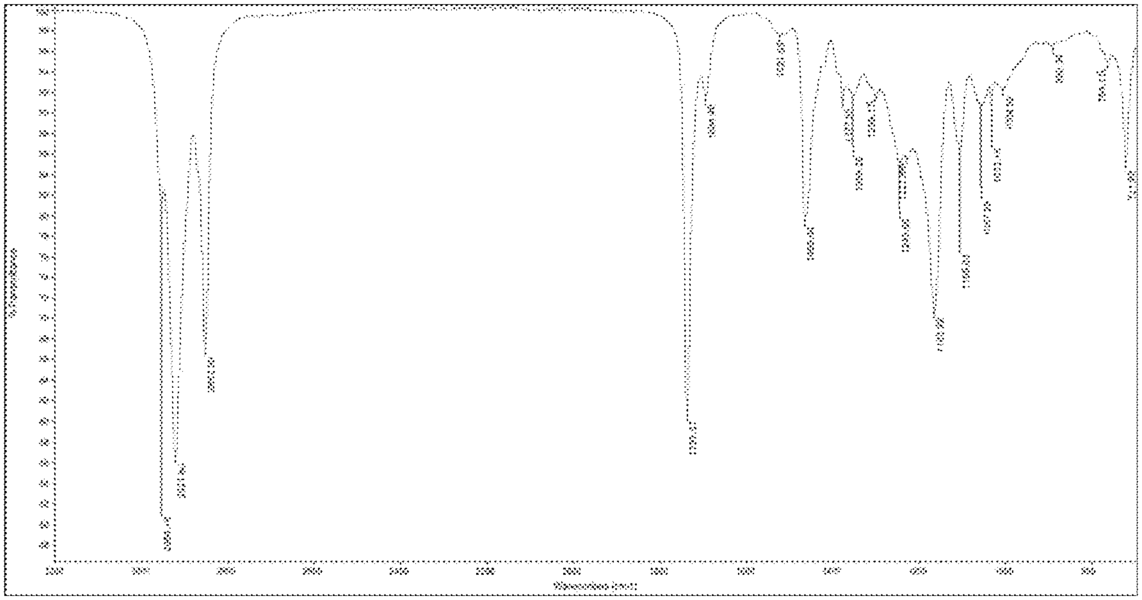
FIG. 7 shows a FTIR spectrograph of dilinoleic acid/dilinoleic diol copolymer based hexamethylene diisocyanate trimer elastomer, as described in embodiments herein.
Figure 8:
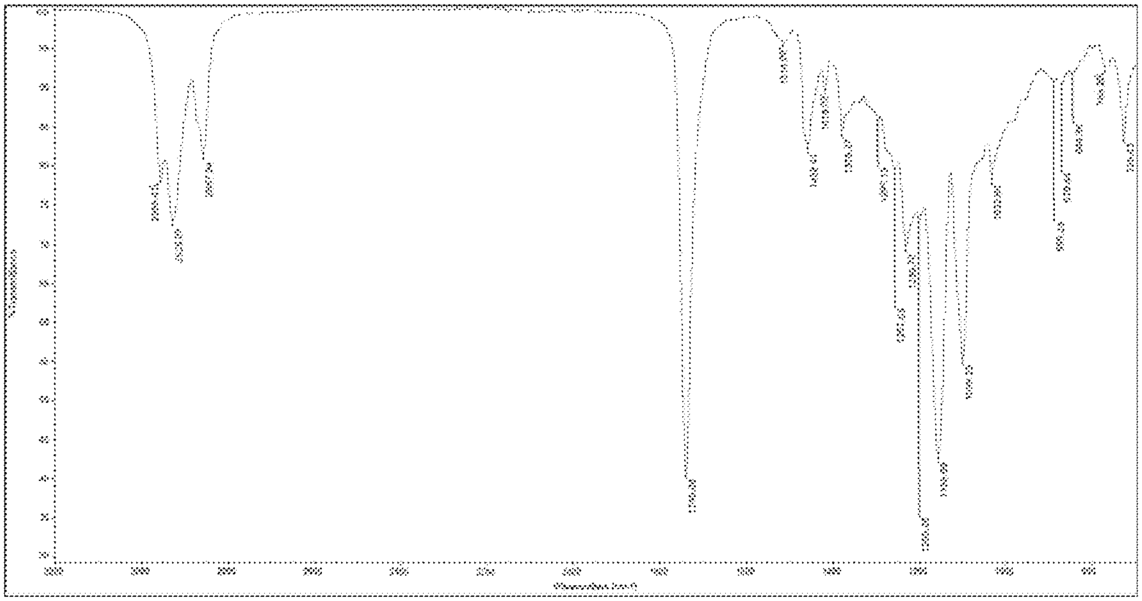
FIG. 8 shows a FTIR spectrograph of castor oil based isophorone diisocyanate trimer elastomer, as described in embodiments herein.

The FTIR spectrograph of castor oil based isophorone diisocyanate trimer elastomer is shown in FIG. 7.

The invention claimed is:

1. A gel composition comprising a polyurethane elastomer gel containing a reaction product of:

(A) a polyisocyanate or a mixture of polyisocyanates comprising two or more isocyanate functional groups;

(B) a polyol or mixture of polyols comprising two or more hydroxyl functional groups;

(C) polyurethane reaction catalyst; and (D) topically acceptable carrier fluid acting as a solvent, the topically acceptable carrier fluid being selected from the group consisting of esters, triglycerides, hydrocarbons, oils, and combinations thereof, and the solvent being acceptable for cutaneous surfaces;

wherein the reaction product has an elastomeric matrix with the topically acceptable carrier fluid entrapped in the elastomeric matrix; and wherein the composition is silicone-free.

2. The gel composition of claim 1, wherein the topically acceptable carrier fluid comprises diisooctyl succinate, heptyl undecylenate, neopentyl glycol diheptanoate, coco-caprylate/caprate, triheptanoin, caprylic/capric triglyceride, dodecane, tridecane, C13-15 alkane, squalene, squalene, isoamyl laurate, isopentyl laurate, caprylic/capric/myristic/stearic triglyceride, caprylic/capric/succinic triglyceride, isopropyl myristate, jojoba esters, tricaprylin, palm oil or combinations thereof.

3. The gel composition of claim 1, wherein a pharmaceutically active ingredient is dissolved in the topically acceptable carrier fluid.

4. The gel composition of claim 1, wherein the polyurethane reaction catalyst is a bismuth group containing catalyst.

5. The gel composition of claim 1, wherein greater than 50% of the carbon content of the topically acceptable carrier fluid is derived from one or more plant sources.

6. The gel composition of claim 1, wherein the polyol is a branched $C_{36}$ dicarboxylic acid/diol copolymer.

7. The gel composition of claim 6, wherein the branched $C_{36}$ dicarboxylic acid/diol copolymer is dilinoleic acid/propane diol copolymer or dilinoleic acid/dilinoleic diol copolymer.

8. The gel composition of claim 1, wherein the composition is in the form of a sunscreen, an oil-in-water emulsion, or a water-in-emulsion.

9. A gel composition comprising a polyurethane elastomer gel containing a reaction product of:

(A) castor oil, dilinoleic acid/propane diol copolymer, or dilinoleic acid/dilinoleic diol copolymer;

(B) isophorone diisocyanate, pentamethylene diisocyanate trimer or hexamethylene diisocyanate trimer, wherein a molar ratio of isocyanate groups to hydroxyl groups is about 1:1 to about 1:2;

(C) polyurethane reaction catalyst; and (D) topically acceptable carrier fluid acting as a solvent at a concentration of 60% (w/w) to 99.9% (w/w) of the gel composition, the topically acceptable carrier fluid being selected from the group consisting of esters, triglycerides, hydrocarbons, oils, and combinations thereof, and the solvent being acceptable for cutaneous surfaces;

wherein a personal care or healthcare active ingredient is optionally incorporated into the polyurethane elastomer gel by dissolving the personal care or healthcare active ingredient in the topically acceptable carrier fluid during formation of the polyurethane elastomer gel, or by admixing the personal care or healthcare active ingredient with a formed polyurethane elastomer gel;

wherein the reaction product has an elastomeric matrix with the topically acceptable carrier fluid entrapped in the elastomeric matrix; and wherein the composition is silicone-free.

10. The gel composition of claim 9, wherein the topically acceptable carrier fluid comprises diisooctyl succinate, heptyl undecylenate, neopentyl glycol diheptanoate, and coco-caprylate/caprate or combinations thereof.

11. The gel composition of claim 9, wherein a pharmaceutically active ingredient is dissolved in the topically acceptable carrier fluid.

12. The gel composition of claim 9, wherein the polyurethane reaction catalyst is a bismuth group containing catalyst.

13. The gel composition of claim 9, wherein greater than 50% of the carbon content of the topically acceptable carrier fluid is derived from one or more plant sources.

* * * * *